United States Patent
Sidoryk et al.

(10) Patent No.: US 11,407,704 B2
(45) Date of Patent: Aug. 9, 2022

(54) PROCESS OF VITAMIN K₂ DERIVATIVES PREPARATION

(71) Applicant: SIEC BADAWCZA LUKASIEWICZ—INSTYTUT CHEMII PRZEMYSLOWEJ IMIENIA PROFESORA IGNACEGO MOSCICKIEGO, Warsaw (PL)

(72) Inventors: Katarzyna Sidoryk, Warsaw (PL); Marek Napiorkowski, Warsaw (PL); Agnieszka Burzynska-Prajzner, Zawiercie (PL); Marcin Cybulski, Warsaw (PL); Marek Kubiszewski, Ilow (PL); Kamil Jatczak, Pruszkow (PL); Lukasz Jedynak, Ozarow Marowiecki (PL); Jerzy Winiarski, Warsaw (PL); Dorota Pietrzkowska, Skierniewice (PL); Konrad Zielinski, Warszawapl (PL)

(73) Assignee: Siec Badawcza Lukasiewicz-Instytut Chemii Przemyslowej imienia Profesora Ignacego Moscickiego, Warsaw (PL)

( * ) Notice: Subject to any disclaimer, the term of this patent is extended or adjusted under 35 U.S.C. 154(b) by 45 days.

(21) Appl. No.: 17/045,477

(22) PCT Filed: Apr. 6, 2019

(86) PCT No.: PCT/PL2019/000026
§ 371 (c)(1),
(2) Date: Oct. 5, 2020

(87) PCT Pub. No.: WO2019/194690
PCT Pub. Date: Oct. 10, 2019

(65) Prior Publication Data
US 2021/0317060 A1 Oct. 14, 2021

Related U.S. Application Data

(60) Provisional application No. 62/829,073, filed on Apr. 4, 2019, provisional application No. 62/653,672, filed on Apr. 6, 2018.

(51) Int. Cl.
C07C 46/04 (2006.01)

(52) U.S. Cl.
CPC .......... *C07C 46/04* (2013.01); *C07C 2602/10* (2017.05)

(58) Field of Classification Search
None
See application file for complete search history.

(56) References Cited

U.S. PATENT DOCUMENTS 3,957,763 A * 5/1976 Chodnekar .......... C07D 311/58
549/408

FOREIGN PATENT DOCUMENTS

| CN | 1218918 C | 9/2005 |
| WO | 2014/058330 A2 | 4/2014 |

OTHER PUBLICATIONS

International Search Report received in international application No. PCT/PL2019/000026, dated Jun. 25, 2019.
Okochi et al., "New Enantioselective Synthesis of (10R,11S)-(1)-Juvenile Hormones I and II," Eur. J. Org. Chem. 2001, No. 11, pp. 2145-22150.

* cited by examiner

Primary Examiner — Joseph R Kosack
(74) Attorney, Agent, or Firm — McBee, Moore & Vanik IP, LLC; Susan E. Shaw McBee; David Vanik

(57) ABSTRACT

Provided is an improved process of vitamin K2 derivatives preparation, represented by formula (I) wherein n is an integer from 3 to 13.

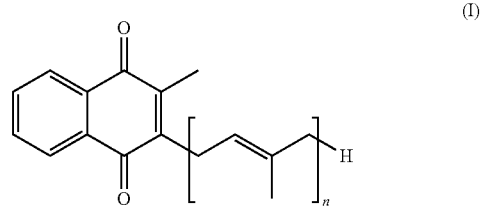

(I)

18 Claims, No Drawings

PROCESS OF VITAMIN $K_2$ DERIVATIVES PREPARATION

FIELD OF THE INVENTION

The present invention relates to the process of vitamin $K_2$ derivatives preparation.

Vitamins $K_2$ play an important role in the blood coagulation cascade and bones supplementation. Synthetic vitamins $K_2$ could be used as the active ingredients of the drug products as well in the dietary supplements.

BACKGROUND OF THE INVENTION

Vitamins $K_2$, called menaquinones (MK-n) or pharnoquinones, are characterized by the menadione structure with a polyprenyl side chain at C-3 position consisting of a different number of isoprene units in the side chain (n=1-13). They are represented by the formula depicted below:

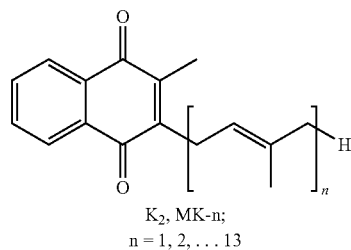

$K_2$, MK-n; n = 1, 2, ... 13

Different biological activity and bioavailability of menaquinones result from the chain length and the number of unsaturated bonds present in that side chain [*Chemistry of Natural Compound* 2007, 43(3), 277-281].

Vitamin K, as a cofactor of γ-carboxylase, is involved in posttraslational γ-carboxylation of certain glutamate residues in precursor proteins PIVKA. Vitamin K is necessary for the biosynthesis and maintaining, at an appropriate level, coagulation factors II, VII, IX and X, osteocalcin, osteopontin, osteonectin and also calcium binding protein in kidneys, placenta and lungs. Vitamin K is involved in the coagulation cascade in animals and its presence is essential for the proper synthesis of blood clotting proteins participating in the coagulation homeostasis. It also contributes to strong bones formation, preventing osteoporosis development. Vitamin K also exerts anti-bacterial, anti-fungal, anti-inflammatory and pain relief activities. Recently, it has been proved that vitamin $K_2$ may substantially affect the condition of arterial walls and blood circulation.

Among other vitamins $K_2$, MK-7 form is of special interest.

It is characterized by better bioavailability and efficacy than other vitamins K. It is also characterized by the high absorption in the small intestine and sustained presence in the blood serum (up to 3 days). Even small daily doses of vitamin MK-7 are sufficient to provide all cells and tissues with vitamin K dependent enzymes and proteins at an appropriate level. On account of its participation in calcium metabolism, vitamin MK-7 is indirectly involved in strong bones formation. Unlike vitamin $K_1$, it also influences arterial vessel wall condition.

Vitamin MK-7 structure consists of the naphthalenedione ring (menadione) with the attached alkyl chain comprising seven isoprene units (heptaprenyl), thus it contains seven double bounds of trans configuration. Considering its molecular structure, synthetic vitamin MK-7 could be synthesized from menadione or its protected derivative, menadiol, following one of the strategies mentioned below:

1. attachment of the heptaprenyl chain directly to the menadiol molecule, according to the so called "0+7" strategy;
2. attachment of the chain's shorter fragments to the monoprenyl derivative of menadiol, according to the "1+n+m" strategy;
3. attachment of the hexaprenyl chain to the monoprenyl derivative of menadiol, according to the "1+6" strategy.

The U.S. Pat. No. 4,199,531 discloses the process of the elongation of the side chain of the menadiol derivative with 1 to n terminal activated isoprenyl units at position C-3, accomplished by its stereo- and regio-selective alkylation with an activated side chain precursor consisting of m isoprenyl units. The carbanion generated under basic conditions on the carbon atom adjacent to the arylthio, arylsulfinyl or arylsulfonyl terminal group of one substrate is subsequently alkylated with alkyl halide as the second substrate. Then, in the case of the reaction of the monoprenylmenadiol arylsulfonyl derivative with polyprenyl halide, the product is subjected to reductive desulfonylation, deprotection of the hydroxyl groups if there is a need thereof, and/or oxidation to afford a menaquinone derivative. According to the specification, alkylation is performed under basic conditions, in the presence of bases such as buthyllithium or phenyllithium, under dry conditions; in a solvent such as tetrahydrofurane, ether or 1,2-dimethoxyethane; at the −78° C. to 20° C. temperature range.

The above mentioned process of the alkylation of the phenylsulfonyl derivative of monoprenylmenadiol using triprenyl halide yielding vitamin MK-4 (according to "1+3 strategy") has been described in *J. Org. Chem.* 2003, 68, 7925. There has also been disclosed the synthesis of the phenylsulfonyl derivative of monoprenyl menadiol dimethoxy-ether (MK-1) from menadiol.

In the International Patent Application WO 2011/117324, a multi-step process of the preparation of polyisoprenyl alcohols and halides with chains of different length in the

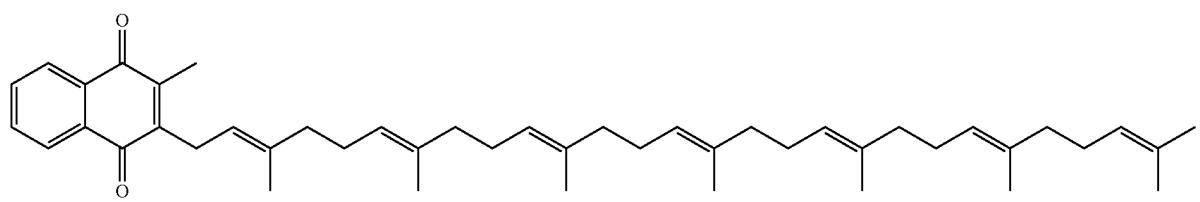

MK-7

Biellmann type reaction has been disclosed. The coupling reaction of the arylsulfonyl or arylthiol polyisoprenyl derivative comprising p isoprenyl units (p=0-4) with the properly protected (for example with acetyl groups) primary polyisoprenyl halide having q isoprenyl units (q=0-4) is carried out in the presence of a non-nucleophilic base. Subsequent removal of SO$_2$Ar or SAr group under reductive conditions, followed by the deprotection of the hydroxyl group, furnishes the desired product. In Example 6, synthesis of pentaprenyl alcohol from diprenyl-alcohol bromide comprising protected acetyl and phenylsulfonyltriprenyl groups is described. After each step of the process: alkylation, desulfonylation and removal of hydroxyl protecting groups, purification of the product by silica gel flash chromatography is necessary. Polyprenyl halides obtained according to this procedure have been used in the vitamins K$_2$ synthesis, in particular vitamin MK-7 synthesis, under Grignard/Kumada or Suzuki conditions, following the "0+7" or "2+5" strategy.

WO 2010/03500 discloses the synthesis of vitamin K$_2$ that is based on the polyprenyl ring attachment to the protected activated menadiol derivative, under Grignard/Kumada or Suzuki conditions, according to the "0+7 strategy".

In both aforementioned International Patent Applications the activated menadione derivative with carbonyl functions protected by alkyl or benzyl groups as the potential synthetic substrate has been claimed. However, in the preparative examples only methoxy-derivatives of menadiol have been used.

WO 2014/058330 discloses the process of the preparation of the MK-7 type of vitamin K$_2$ by coupling the hexaprenyl chain precursor of all-trans configuration with a menadiol derivative bearing the phenylsulfonyl monoprenyl terminal group and protected in the form of alkoxy-ethers, especially in the form of ethoxy-ether. The said phenylsulfonyl monoprenyl menadiol ethoxy-derivative is used in a crystalline form that significantly improves the process of its purification. In the preferred embodiment, in the reaction under the Julia protocol, hexaprenyl bromide is used bearing one side chain phenylsulfonyl group. That group is removed together with the second one resulting from the alkyl addition reaction in one step, thus shortening the synthesis without the deterioration of the yield and purity of the final product.

The previous works on the process for preparation of vitamins MK-7 using "1+6" strategy led us to the conclusion that the key issue is the appropriate selection of the protecting group of the starting menadiol. The appropriately selected group should be stable in the coupling reactions with various polyprenyl chains having different number of isoprene units both under acidic and basic conditions, i.e. in the presence of Lewis acids and/or strong bases. Moreover, the selected group should be prone to cleavage from the advanced intermediate of vitamin K$_2$ in the step of restoration of quinine structure under mild conditions and in a high yield. The literature review of the protecting groups known in the art (R G. M. Wuts, T. W. Greene, Green's Protective Groups in Organic Synthesis. 4$^{th}$ ed., 2007, Wiley & Sons) led us to choose some most promising groups for further process development, like benzyl and lower alkyl groups. However, the experimental works resulted in the failure of the alkylation of menadiol with isopropyl bromide. In turn, the alkylation with benzyl bromide gave the menadiol protected with benzyl group in high yield. This group, however, was unstable under conditions of subsequent coupling reaction with the phenylsulfonyl derivative of isoprenyl bromide.

The aim of the present invention was to develop an alternative, improved process for the preparation of a wide range of synthetic all-trans vitamins K$_2$ with different lengths of the polyisoprenyl side-chains, based on the common structural menadione synthon and starting from easily available and inexpensive natural or semi-synthetic substrates.

Disclosure of the Invention

The aim of the invention has been achieved as the result of protection of the menadiol hydroxyl groups in the form of allyl ether.

Hence the invention relates to the process of preparation of vitamin K$_2$ derivatives, represented by formula (I)

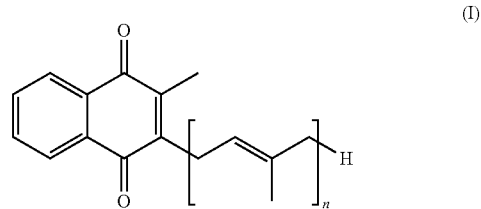

wherein n is an integer from 3 to 13, comprising the steps of:

(a) reacting an α-sulfonyl carbanion generated in situ from the phenylsulfone of menadiol derivative of formula (II)

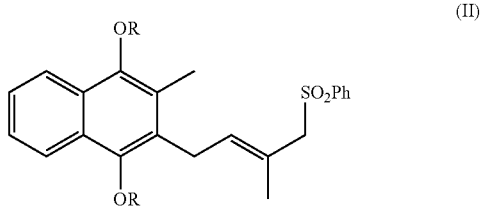

wherein R represents the allyl protecting group, in the presence of a strong organometallic base, with a polyprenyl halide of formula (VII)

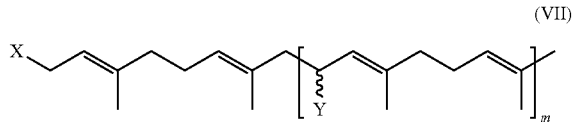

wherein

X is a halogen atom selected from bromine, chlorine and fluorine atoms,

Y is H or —SO$_2$Ph, m is an integer from 0 to 5, as an alkylating agent;

to yield the phenylsulfonyl derivative of menadiol of the formula (VIII)

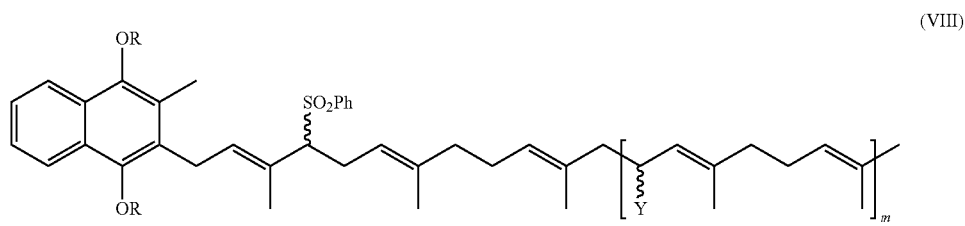

(VIII)

wherein R, Y, and m have the meaning defined above, (b) removing the phenylsulfonyl groups from the menadiol derivative of formula (VIII) by the reductive elimination, to yield the menadiol derivative of formula (IX)

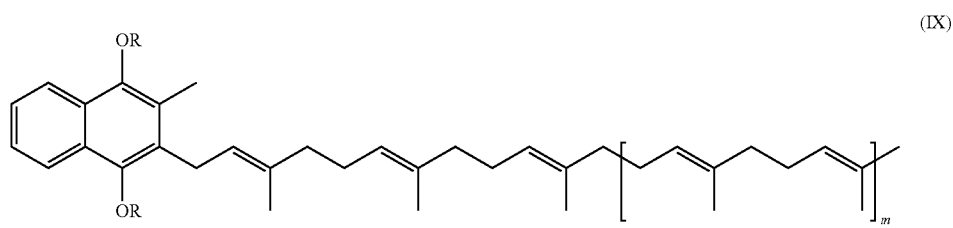

(IX)

wherein R and m have the meaning defined above;

(c) subjecting the menadiol derivative of formula (IX) to an oxidative deeterification, to yield the crude menadione compound of formula (I),

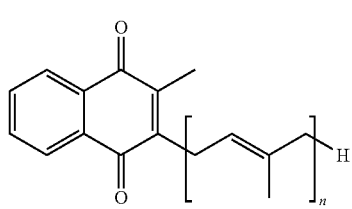

(I)

wherein n is the integer from 3 to 13, and (d) optionally, purifying the crude menadione compound of formula (I) to yield the pure vitamin $K_2$.

The length of the side chain in the target vitamin $K_2$ could be modified by the number of the isoprenyl units of the side chain precursor derived from the natural or semi-synthetic substrate.

In case the target vitamin $K_2$ is MK-7 type of vitamin $K_2$ comprising seven isoprenyl units, the polyisoprenyl chain may be constructed from, e.g., two farnesyl moieties (see, WO 2014/058330), three geranyl moieties, etc.

In case of the other vitamins $K_2$, one could consider using the combination of the above mentioned natural sources of isoprenyl units.

In one embodiment of the invention, the polyprenyl halide used as the alkylaing agent is represented by formula (VII)

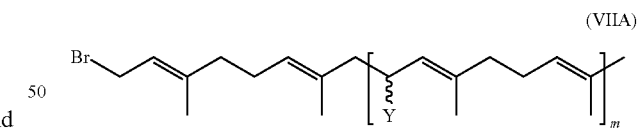

(VII)

wherein

X is a halogen atom,

Y is —$SO_2$Ph, and m is an integer from 0 to 5.

In another embodiment of the invention, the polyprenyl halide used as the alkylating agent is the polyprenyl bromide of formula (VIIA)

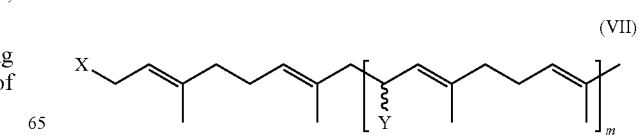

(VIIA)

wherein

Y is H, and m is an integer from 0 to 5.

In the other embodiment of the invention, the polyprenyl halide used as the alkylating agent, represented by formula (VII)

(VII)

wherein

X is a halogen atom,

Y is H or —SO$_2$Ph, m is an integer from 1 to 5, is obtained in the stepwise process of:

(i) coupling the phenylsulfonyl-geranyl unit of formula (III),

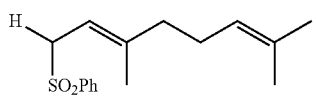
(III)

with the compound of formula (IV)

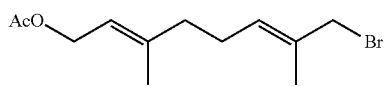
(IV)

and repeating the said coupling process with the use of compound of formula (IV) until the compound of formula (V) of the desired chain length is obtained

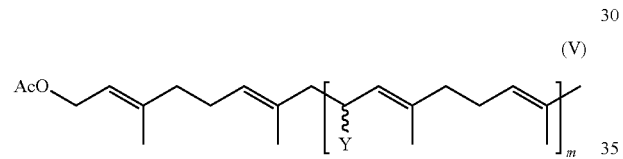
(V)

wherein

Y is —SO$_2$Ph, m is an integer from 0 to 5;

(ii) hydrolysis of the compound of formula (V), to yield the polyisoprenol derivative of formula (VI)

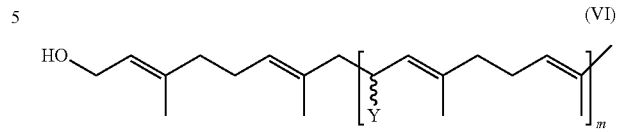
(VI)

wherein Y represents —SO$_2$Ph, and m is an integer from 0 to 5;

(iii) optionally, removing the phenylsulfonyl groups to yield the polyprenyl bromide of formula (VII)

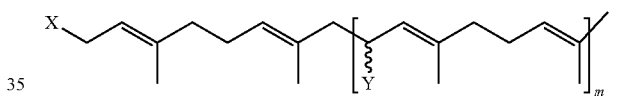
(VII)

wherein Y is H, and m is defined above, and (iv) substituting the hydroxyl group of the compound of formula (VII) for a halogen atom in the reaction with a halogenating agent, to yield the polyprenyl halide of formula (VIII),

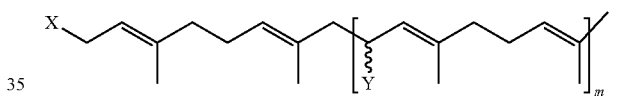
(VIII)

wherein X is a halogen atom,

Y is H or —SO$_2$Ph, and m is defined above.

Further aspects of the invention are the new compounds:

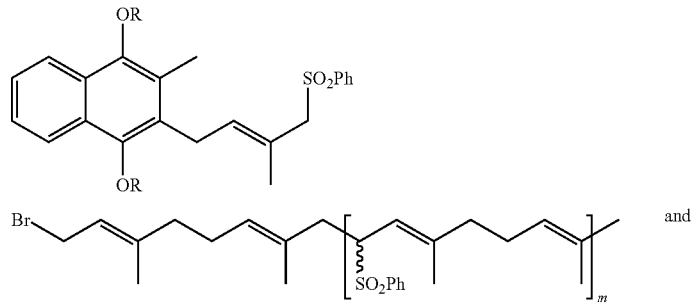
(II)

and

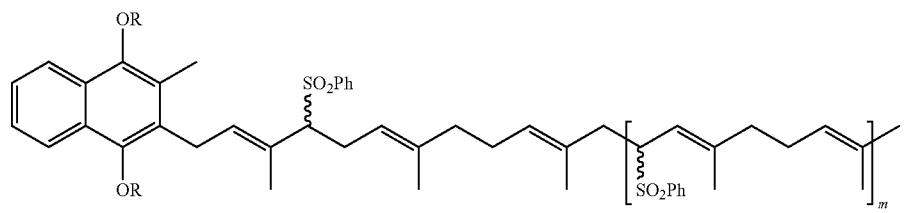

wherein
R is the allyl protecting group, and
m is an integer from 0 to 5.

DETAILED DESCRIPTION OF THE INVENTION

In the process of the present invention, Synthon A is the monoprenyl derivative of menadiol represented by formula (II), wherein R is the allyl protecting group. Due to the presence of the phenylsulfonyl functionalizing group, the monoprenyl group at C-3 can be elongated by coupling an appropriate number of isoprenyl units.

Synthon A can be synthesized in a manner similar to that known in the art (J. Org. Chem. 2003, 68, 7925-27), using commercially available menadione, which is first protected in form of diallyl ether derivative, and then alkylated with (E)-4-chloro-2-methyl-1-phenylsulfonyl-2-butene under Friedel-Crafts conditions. Protection of the hydroxyl groups prevents side reactions, in particular menadiol cyclization, which may occur under Friedel-Crafts conditions.

Typically, the reactions of alkylation are carried out under Friedel-Crafts conditions using Lewis acids catalysts, such as $BF_3 \cdot OEt_2$, $FeCl_3$, $AlCl_3$, $ZnCl_2$, or $InCl_3$.

Referring to the present invention, however, the reaction of diallyloxy menadiol and (E)-4-chloro-2-methyl-1-phenylsulfonyl-2-butene in dichloromethane in the presence of different Lewis acids at the temperatures within the range from 0 to −20° C., resulted only in the decomposition of staring material, diallyloxy menadiol, while the expected product of alkylation was not observed. The problem of starting diallyloxy menadiol instability under the process conditions was resolved via a base addition to the reaction.

Without being bound by any particular theory, while performing Friedel-Crafts reaction, HCl releasing into the reaction medium causes diallyloxy menadiol substrate decomposition resulting in the deallylation product. Only the neutralization of the generated HCl could supress deallylation process of the acid-sensitive diallyloxy menadiol, and give the expected product of alkylation.

Although a wide range of both organic and inorganic bases have been tested, the best results were obtained when using solid inorganic bases (see, Y.G. Si et al. Highly regioselective Friedel-Crafts reactions of electron-rich aromatic-base: Efficient synthesis of pesticide Cycloprothrin. Adv. Synth. Catal. 2006, 348, 898-904).

The effectiveness of the organic bases in the transformation of diallyloxy menadiol into its phenylsulfonyl-isoprenyl derivative has also been examined. Replacing the inorganic base with an organic one, such as triethylamine or pyridine, blocks the reaction.

Thus, in one embodiment of the invention, Synthon A is obtained in the Friedel-Crafts reaction catalysed by the Lewis acid in the presence of the solid inorganic base as the alkylation promoter.

In the preferred embodiment of the invention, Synthon A is obtained in the presence of $InCl_3$ as the Lewis acid, and $Na_2CO_3$ or $K_2CO_3$ as the solid inorganic base, and in the most preferred embodiment of the invention, Synthon A is obtained in the presence of $InCl_3$—solid inorganic base-catalyzed Friedel-Crafts system.

The second starting material in the process of the present invention, Synthon B, is the polyprenyl halide, especially the polyprenyl bromide, represented by the formula (VII) below

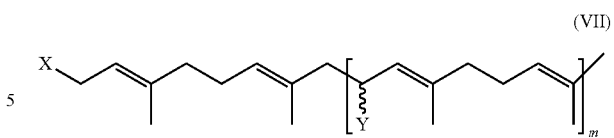

(VII)

wherein
X is a halogen atom,
Y is H or $SO_2Ph$, and
m is an integer from 0 to 5.

It would be appreciated by those skilled in the art that by combining the synthons A and B, the vitamin $K_2$ derivative comprising even or odd number of isoprenyl units could be obtained depending on the number of "m" units in the starting compound of formula (VII).

The key step in the preparation of vitamins $K_2$ according to the present invention is coupling of the A and B synthons, accomplished in the reaction of the nucleophilic addition.

Coupling of A and B synthons results in formation of vitamin $K_2$ derivative possessing one or more phenylsulfonyl groups in the side chain, depending on the substrates used for the construction of the polyprenyl chain.

In one embodiment of the invention, the synthesis of Synthon B, ie. polyprenyl halide of formula (VII), can be accomplished according to the synthetic approach starting from easily available geraniol. Geraniol, (2E)-3,7-dimethyl-2,6-octadien-1-ol, is the chemical compound from the group of unsaturated terpene alcohols, having two unsaturated bonds in configuration trans.

As the result of the repeated alkyl addition reactions using geraniol as the block building material, the even number of isoprenyl units of synthon B could be obtained to be subsequently combined with one isoprenyl unit derived from Synthon A. In effect, vitamin $K_2$ derivative of different polyprenyl chain length could be obtained.

Coupling of isopropenyl chain fragments by way of alkylation of the appropriate sulfones is generally known in the art, among others from J. Org. Chem. 2003, 68, 7925; J. Chem. Soc. Perkin I 1981, 761; J. Org. Chem. 2008, 73, 7197; Tetrahedron 2009, 65, 6310. This reaction can be performed in the presence of a strong base, such as potassium tert-butanolate, n-butyllithium, lithium, sodium or potassium bis(trimethylsilyl)amidate, in a polar aprotic solvent.

The process for preparation of all-trans geranyl-geraniol is disclosed, for example, in CN 1218918 C, and comprises the steps of oxidation of geranyl acetate resulting in the mixture of an alcohol and an aldehyde followed by the reduction of the aldehyde to obtain 8-geranyl-hydroxy-acetate. Then, the said alcohol is transformed to the geranyl bromoacetate by means of $PBr_3$ in pyridine, and finally reacted with the phenylsulfonyl-geraniol with subsequent removal of the phenylsulfonyl group by means of $Li/MeNH_2$.

In the process according to the present invention, the crude product of geraniol oxidation which is obtained in the reaction with the use of a large volume of substrates, is purified by distillation under reduced pressure followed by a simple filtration, as an alternative to other available purification methods, e.g., column chromatography. Moreover, using geraniol acetate as the starting material in the oxidation reaction results in its high regioselectivity. In contrast to the prior art oxidation process using fernesol starting material resulting in the mixture of oxidation constitutional isomers, in the present process the hydroxyl group is mainly formed at the terminal methyl of the geranyl chain.
The synthesis of polyprenyl halide of formula (VII) can be accomplished according to the following synthetic approach, as illustrated in Scheme 1. By way of illustration, the said scheme is provided for the preparation of the compounds of formula (VII), wherein X is Br, Y is —SO$_2$Ph, and m is 2.
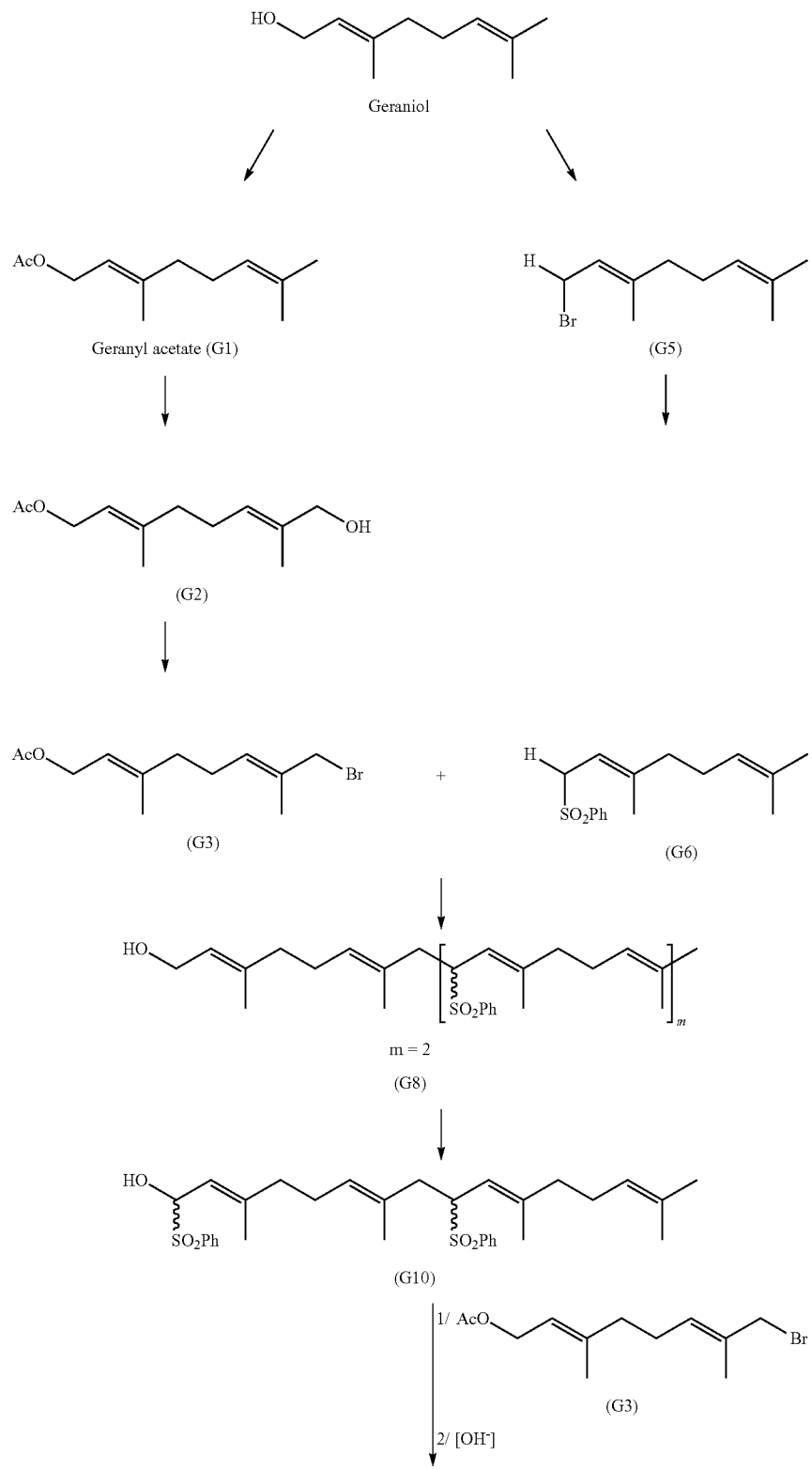

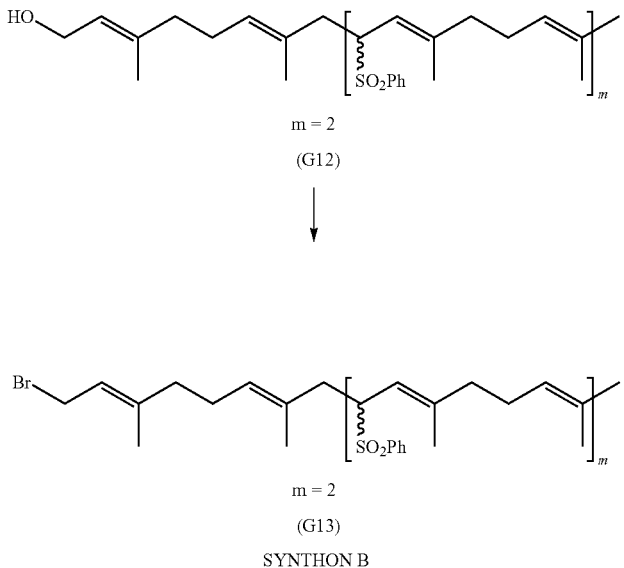

(G12)

↓

(G13)

SYNTHON B

In the first step, geranyl acetate (G1) is used, either commercially available or synthetized from geraniol by acetylation with the use of $Ac_2O$ in pyridine.

The resulting geranyl acetate is oxidized with the use of selenium dioxide to E,E-8-hydroxy-geranyl acetate (G2).

Selenium dioxide ($SeO_2$) mediated incorporation of the oxygen atom at the allylic position is known, for example, from T. Wirth et al., Organoselenium Chemistry, Modern Developments in Organic Synthesis, ed. Springer. According to the present invention, oxidation can be performed using a stoichiometric amount of $SeO_2$, or, preferably, a catalytic amount of $SeO_2$ using acid as co-catalyst, for example salicylic acid or $SiO_2$, in the presence of a 2-3-fold molar excess of co-oxidizer, such as tert-butyl peroxide (in water or an organic solvent) or hydrogen peroxide. In another embodiment of the invention, the oxidation reaction can be accomplished by using $SeO_2$ in the presence of the molar excess of N-oxide N-methylmorpholine. The crude product is purified, e.g. by fractional distillation under reduced pressure.

E,E-8-Hydroxygeranyl acetate (G2) is converted into its halide, especially bromide (G3), using commonly known halogenating agents. Suitable halogenating agents include, for example, SOCl2 or HCl (gaseous) converting the hexaprenol into its corresponding chloride, PBr3 or HBr—into bromide and PPh3/I2, PI3 or HI—into iodide.

Independently, geraniol is transformed into its halide, especially bromide (G5).

Geraniol halide (G5) is treated with sodium benzenesulfinate to give geranyl phenyl sulfone (G6).

Bromide derivative of geranyl acetate (G3) is coupled in the alkylation reaction with geranyl phenyl sulfone (G6) followed by a hydrolysis to give compound (G8).

Coupling of the polypropenyl chain fragments by way of alkylation of the appropriate sulfones is generally known in the art, among others from J. Org. Chem. 2003, 68, 7925; J. Chem. Soc. Perkin I 1981, 761; J. Org. Chem. 2008, 73, 7197; Tetrahedron 2009, 65, 6310. This reaction can be performed in the presence of a strong base, such as potassium tert-butanolate, n-butyllithium, lithium, sodium or potassium bis(trimethylsilyl)amidate, in a polar aprotic solvent.

The phenylsulfonyl polyprenol (G8) is transformed by a two-step synthesis into the polyprenol derivative (G10), with two phenylsulfonyl groups $SO_2Ph$.

The resulting compound (G8) can be converted into the phenylsulfonyl derivative (9), which can be subject to the alkylation reaction with geranyl acetate bromide (3) for further elongation of the chain or, either directly or after removal of the phenylsulfonyl groups, converted into halide of formula (VII), wherein all Y substituents represent phenylsulfonyl groups $SO_2Ph$.

Geranyl phenyl sulfone (G10) is coupled in the alkylation reaction with the second molecule of geranyl acetate bromide (G3) followed by a hydrolysis to give compound (G12). The resulting compound (G12) can be de-sulfonated to obtain the compound of formula (VII) where Y is H, and subsequently converted into its halide wherein the substituents Y and m have the defined meaning.

Suitable halogenating agents are, for example, $SOCl_2$ or HCl (gaseous) converting the hexaprenol into the corresponding chloride, $PBr_3$ or HBr—into bromide and $PPh_3/I_2$, $PI_3$ or HI—into iodide.

Alternatively, compound (G12) may be directly converted into its halide (G13) which can be used as Synthon B in the key step of vitamin $K_2$ synthesis.

The processes of the prenyl fragments coupling and hydrolysis of the phenylsulfonyl polyprenyl acetates can be accomplished successively, following isolation and purification of the compounds. In the preferred embodiment of the invention, however, the steps of the prenyl chain fragments coupling and further hydrolysis are carried out successively as an "one pot" reaction (i.e. G8, G12).

The preferred embodiment of the process of Synthon A and Synthon B coupling resulting in the MK-7 type of vitamin $K_2$ is illustrated in Scheme 2 below.

Scheme 2. MK-7 type of vitamin K$_2$ synthesis
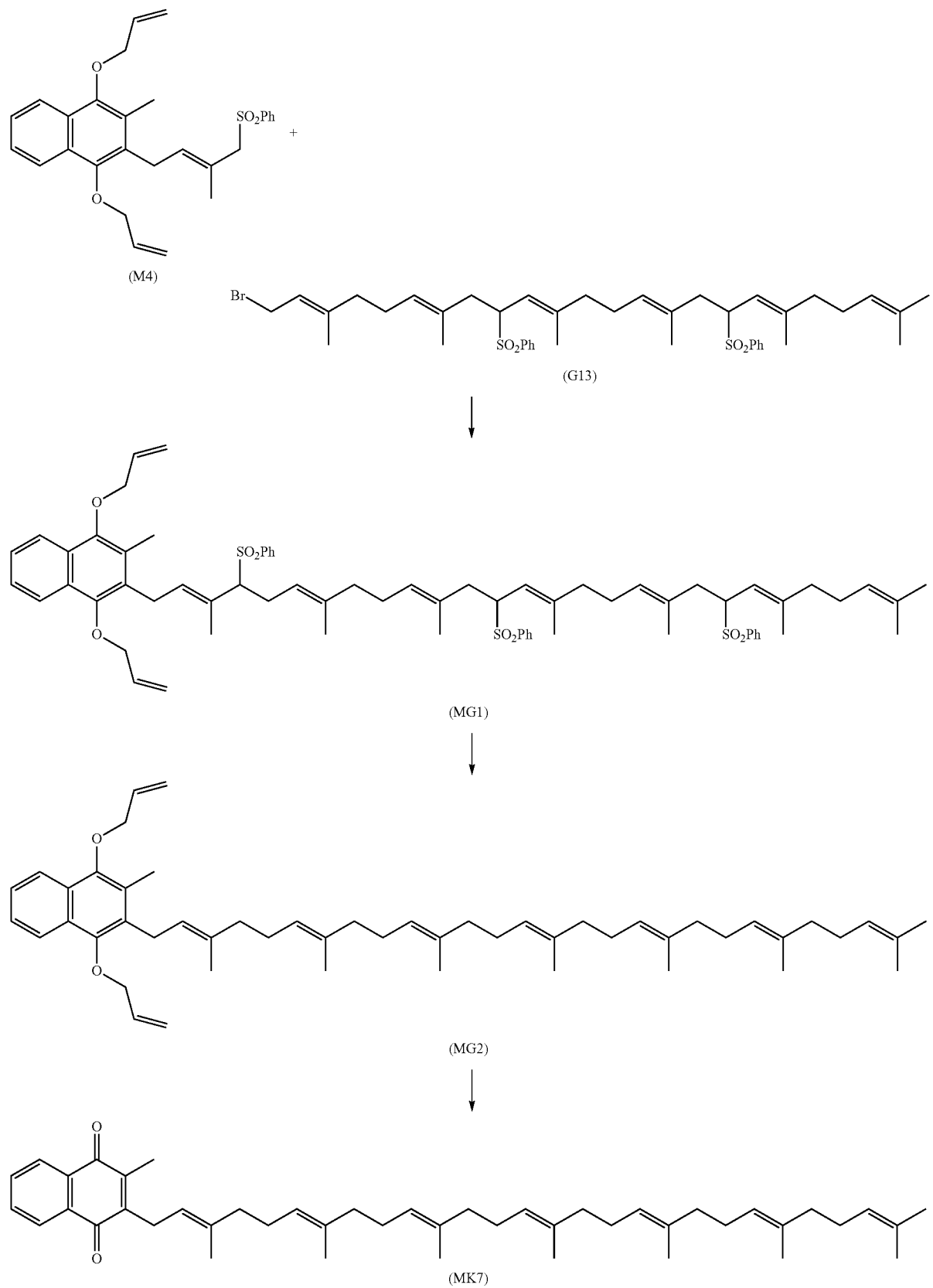

In order to couple Synthon B with Synthon A, from the menadiol derivative of formula (M6), α-sulfonyl carbanion is generated in situ in the presence of an organometallic strong base. The formation of stable —CH—SO$_2$—Ar carbanions due to the activation of the (arylsulfonyl)methylene group under basic conditions was disclosed in some publications, among others, P. E. Magnus, Tetrahedron 33 (1977), 2019; B. M. Trost, Bull. Chem. Soc. Jpn. 61 (1988), 107; N. S. Simpkins, Tetrahedron 46 (1990), 6951. To generate carbanions, bases such as n-butyllithium, potassium tert-butanolate, lithium or sodium bis(trimethylsilyl)amidate (Me$_3$-Si—N(M)-Si-Me$_3$, M=Li, Na, K) and lithium or sodium diisopropylamidate were used, as has been described in the publication by I. R. Baldwin, R. J. Whitby Chem. Commun. (2003), 2786-2787.

In one embodiment of the invention, sulfonyl carbanion is generated using alkali metal bis(trimethylsilyl)amidates, most preferably, sodium bis(trimethylsilyl)amidate (HMDSNa), that results in high region-selectivity and reaction yields. The reaction is carried out in a polar aprotic solvent, such as tetrahydrofuran, dimethylformamide, hexamethylphosphoramide or the mixture thereof.

In the other embodiment of the invention, sulfonyl carbanion is generated using potassium tert-butanolate (t-BuOK).

The coupling reaction is carried out in a polar aprotic solvent, such as tetrahydrofuran, dimethylformamide, hexamethylphosporamide or the mixture thereof.

The allyl protected groups are stable under these conditions, and the coupling products are isolated in good yields.

It has been unexpectedly found that the use in the process according to the present invention of bromides of formula (VII) substituted with one or more phenylsulfonyl substituents gives better results than the use of unsubstituted polyprenyls.

In case of alkylation of allyl-protected menadiol with hexaprenyl bromide of formula (VII), wherein Y is H, the formation of various undesirable impurities was observed. By way of example, the impurity (IMP 1) has been isolated by column chromatography from the crude product of reaction. This impurity was not observed in the reaction of hexaprenyl bromides of formula (VII), wherein one or two phenylsulfonyl groups Y are present, probably due to their ability to prevent this type of side reaction.

In one embodiment of the invention, all phenylsulfonyl groups present in polyprenyl chain are removed simultaneously after completion of Synthons A and B coupling reaction.

The methods of removal of arylsulfonyl groups of substituted (arylsulfonyl)alkanes are known in the art. They can be removed under different reductive conditions, depending on molecular structure of the substrate (Y. Liu, Y. Zhang, Org. Prep. Proc. Int. 33 (2001), 372). Among general methods, reduction with alkali metals dissolved in liquid ammonia (for example J. R. Hwu at al., J. Org. Chem. 61 (1996), 1493-1499); reduction with Mg/MeOH or Mg/EtOH+HgCl$_2$ (G. H. Lee at al., Tetrahedron Lett. 34 (1993), 4541-2; A. C. Brown, L. A. Carpino, J. Org. Chem. 50 (1985), 1749-50) and with sodium amalgam in MeOH, buffered with Na$_2$HPO$_4$ (B. M. Trost at al., Tetrahedron Lett. 17 (1976), 3477-8) should be mentioned.

In the prior art processes (eg., WO 2014/058330), the phenylsulfonyl groups are removed in the reaction of reductive elimination with borohydrides of alkali metals, such as sodium or potassium, using complexes of metal (II) dihalides with phenylphosphite type bidentate ligands of the formula [M{Ph2P(CH$_2$)nPPh$_2$}X$_2$], wherein n=2-5, X=Cl or Br and M=Co, Ni or Pd as catalysts. As the preferred catalysts, metal borohydrides were mentioned, unsubstituted or substituted, having up to three substituents selected among C$_{1-5}$-alkyl and phenyl, such as lithium triethylborohydride, lithium tri-sec-butylborohydride, tri-sec-butyllithium, sodium or potassium, potassium triphenylborohydride. Most preferably, lithium triethyloborohydride in presence of Pd(dppe)Cl$_2$ complex, where dppe represents 1,2-bis(diphenylphosphino)ethane or Pd(dppp)Cl$_2$, where dppp represents 1,3-bis(diphenylphosphino)propane.

In the process of the present invention, due to the use of the allyl protecting groups, the phenylsulfonyl groups could be removed under much more milder conditions.

Preferably, the phenylsulfonyl groups are removed with sodium amalgam in MeOH, buffered with Na$_2$HPO$_4$, while the allyl groups are left intact.

As a result of this approach, wherein all phenylsulfonyl groups are simultaneously removed from the resulting triphenylsulfonyl derivative of menadiol of the formula (VIII) (MG1 in Scheme 2), vitamin K$_2$ could be obtained in unexpectedly high yield and in limited number steps process, which effects in the reduction of time and expensive reagents consumption.

In the last step of synthesis, the compound of the formula (IX) is subjected to oxidative deeteryfication (deallylation), to restore the quinine structure of the starting menadione.

Oxidation of the phenolic groups to the quinine structures could be typically accomplished by use of one of the common oxidizing agents, such as chromium trioxide in acetic acid, sodium dichromate or Fremy's salt, ie. potassium nitrosodisulfonate.

In one embodiment of the present invention, cerium ammonium nitrate (CAN) is used as the oxidizing agent. CAN is known, for example, from J. Org. Chem. 2003, 68, 7925-27.

In the processes known in the art, the oxidative deallylation is typically carried out by removal of allyl groups in a two-step procedure. First, the isomerization of an olefin group to a vinyl one with a strong base or a metal catalyst, such as Pd/C, (Ph$_3$P)RhCl, or [Ir(COD)(PMePh$_2$)$_2$PF$_6$, is performed. Next, the vinyl ether is removed by either H$^+$ or Hg$^{2+}$ catalysed hydrolysis or oxidative cleavage. The most popular strategies for allyl ether deprotection involve the usage of Pd(PPh$_3$)$_4$, or Pd/C (P. G. M. Wuts, T. W. Greene. Green's Protective Group in Organic Chemistry. 2007, ed. Wiley) in combination with reagents such as LiBH$_4$, NaBH$_4$, p-TsOH (K. S. Babu et al., A simple, effective and highly selective cleavage of 3-methylbut-2-enyl(prenyl)ethers using p-toluenesulfonic acid. Chem. Lett. 32, 8, 2003, 704-705), K$_2$CO$_3$ (D. R. Vutukuri et al., A mild deprotection strategy for allyl-protecting groups and its implications in sequence specific dendrimer synthesis. J. Org. Chem. 2003, 68, 1146-1149), and KOH (M. Ishizaki et al., Palladium charcoal-catalyzed deprotection of O-allylphenols. Tetrahedron 60, 2004, 7973-7981). Further, the allyl groups deprotection followed by in situ oxidation of hydroxyl to carbonyl group could be completed using the catalytic amounts of CrO$_3$ and a molar excess of 70% t-BuOOH (S. Chandrasekhar et al., One pot deprotective oxidation of O-allyl ethers using 70% tert-butyl hydroperoxide and catalytic CrO$_3$. Synlett. 7, 1999, 1063-1064).

In the preferred embodiment of the present invention, allyl groups are removed and the at the same time menadiol moiety is oxidized (oxidative deallylation) using Pd(OAc)$_2$/Ph$_3$P and 1,3-dimethylbarbituric acid. In this reaction, 1,3-dimethylbarbituric acid acts as the "scavenger" of allyl groups, avoiding formation of the by-products. The reaction of oxidative deallylation can be carried out at the temperatures between the room temperature to 40° C. The increase of the reaction temperature to 40° C. shortens the time of oxidative deallylation to about 20-30 min. (TLC).

The crude vitamin $K_2$ product (I) obtained in the process of the invention could be isolated, for example by column chromatography, and then it may be purified, for example by high performance liquid chromatography, and/or by crystallization.

In the preferred embodiment of the invention, the crude MK-7 type of vitamin $K_2$ is purified by the column chromatography, and crystallized in the mixture of ethyl acetate and ethanol.

The process of vitamin $K_2$ derivatives preparation according to the present invention enables the preparation of different types of vitamin $K_2$ using easily available starting compounds, and providing the desired all-trans configuration of double bonds that conforms with the configuration of the starting A and B synthons.

The all-trans structure of MK7 type of vitamin $K_2$ could be confirmed by recording the $^{13}C$ Nuclear Magnetic Resonance spectra, while at the same time the presence of cis isomers could be excluded. In the all-trans form, there is observed the specific $^{13}C$ chemical shift of the $CH_2$ group in the trans-position at about 40 ppm and simultaneously the $CH_3$ group in the cis-position at about 16 ppm. In the cis form of MK7 type of vitamin $K_2$, the $^{13}C$ chemical shift of the $CH_2$ group in the cis-position is about 32 ppm and the $CH_3$ group in the trans-position is about 23 ppm. $^{13}C$ NMR spectrum recorded for MK7 type of vitamin $K_2$ obtained by the process according to the invention shows the presence of the signals characteristic for trans form only, thus confirming the all-trans structure of the product.

In the preferred embodiment of the process according to the present invention, α-sulfonyl carbanion of monoprenyl menadiol of formula (II) is alkylated with hexaprenyl bromide of formula (VII), wherein Y represents the phenylsulfonyl groups —$SO_2Ph$. All phenylsulfonyl groups are simultaneously removed from the resulting diphenylsulfonyl derivative of menadiol of formula (VIII) under mild conditions with sodium amalgam, and after that the menadione structure is restored. As the result of this approach, vitamin MK-7 is obtained in unexpectedly high yield and in much shorter process as compared to the prior art methods, thereby affecting in reduction of time, solvents and expensive reagents consumption.

The present invention is illustrated by the following non-limiting examples.

EXAMPLES $^1H$ and $^{13}C$ NMR spectra were measured in $CDCl_3$ using a Varian-NMR-vnmrs500 spectrometer at 298 K. Standard experimental conditions and standard Varian programs were used. To assign the structures under consideration, the following 1D and 2D experiments were performed: the 1D selective NOESY, and 2D gradient selected COSY, $^1H$-$^{13}C$ HSQC and $^1H$-$^{13}C$ HMBC. The $^1H$ and $^{13}C$ NMR chemical shifts relate to the TMS. The concentration of all solutions used for the measurements was about 10-20 mg of the compounds in 0.6-0.8 cm$^3$ of the solvent.

Mass spectra were acquired with:
  quadrupole mass spectrometer, ESI LCMS-2010 (Shimadzu, Duisburg, Germany). Software: LCMS solution v. 2.05.

HPLC combined with a pair of two pumps LC-10AD$_{VP}$, autosampler SIL-HT$_4$, column thermostat CTO-10$_4$ degasser DGU-20$_{A3}$ (Shimadzu, Duisburg, Germany)

The progress of the reactions was monitored by thin layer chromatography (TLC) with Merck DC-Alufolien Kieselgel 60 $F_{254}$. Column chromatography was performed on Merck silica gel 60 (230-400 mesh).

Example 1

8-Hydroxy-geranyl acetate (G2)

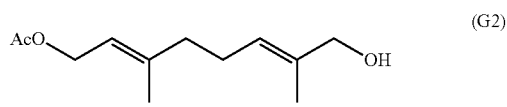

The solution of tert-butyl hydroperoxide in water (70%, 9.40 mL) was added to the suspension of $SeO_2$ (210 mg, 1.89 mmol) and salicylic acid (261 mg, 1.89 mmol) in $CH_2Cl_2$ (50 mL) and stirring was continued at RT. After 30 min. the mixture was cooled down to 0° C. and the solution of geranyl acetate (5.0 g, 25.4 mmol) in $CH_2Cl_2$ (5 mL) was added dropwise. The resulting mixture was stirred at 0° C. for 5 min., then at RT for 24 h. The solvent was removed under vacuum, the residue was dissolved in $Et_2O$ (50 mL). The organic phase was washed with the saturated $Na_2S_2O_3$ aq. solution, water and brine, dried over anhydrous $Na_2SO_4$, filtered and evaporated to dryness under vacuum. The oily residue was dissolved in methanol (40 mL), the solution was cooled to −10° C. and at this temperature $NaBH_4$ (0.15 g, 40 mmol) was added portionwise during 15 min. After 30 min., the cold saturated $NH_4Cl$ aq. (50 mL) solution was added and the product was extracted with $CH_2Cl_2$ (3×50 mL). The combined organic extracts were washed with water and brine, dried over anhydrous $Na_2SO_4$, filtered and evaporated to dryness. The residue was purified by distillation (p=0.04 mbar, 70° C.) to give (2E,6E)-8-hydroxy-3,7-dimethylocta-2,6-dien-1-yl acetate G2 (oil, 3.2 g, 15.02 mmol, 59%). A sample for the NMR study was purified by column chromatography.

$^1H$ NMR (CDCl$_3$, 500 MHz) δ 5.38-5.33 (m, 2H, —CH=CH$_2$—), 4.59 (d, 2H, —O—CH$_2$—CH=), 3.99 (s, 211, CH$_2$—OH), 2.20-2.15 (m, 2H, —CH$_2$—CH$_2$—CH=), 2.11-2.08 (m, 2H, —CH$_2$—CH$_2$—CH=), 2.06 (s, 3H, CH$_3$—COOR), 1.71 (s, 3H, —CH$_3$), 1.67-1.62 (m, 4H);

$^{13}C$ NMR (CDCl$_3$, 125 MHz) δ 171.2, 141.7, 135.2, 125.2, 118.6, 68.8, 61.4, 39.0, 25.6, 21.0, 16.35, 13.63.

Example 2

Geranyl Sulfone (G6)

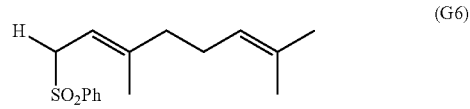

PBr$_3$ (0.42 mL, 1.2 g, 4.5 mmol) was added dropwise at 0° C. to the solution of geraniol (1 g, 6.50 mmol) in anhydrous THF. The resulting mixture was stirred at 0° C. for 3 h. The reaction was quenched by adding iced water. The organic layer was separated, and the water phase was extracted with diethyl ether (3×10 mL). The combined organic extracts were washed with saturated NaHCO$_3$ aq. solution and brine, dried over anhydrous Na$_2$SO$_4$, filtered and evaporated under vacuum to give geranyl bromide G5 as colorless oil (1.2 g, 5.55 mmol, 86%). Crude product G5 was dissolved in anhydrous DMF (15 mL) and PhSO$_2$Na (3 g, 18.3 mmol) was added. The solution was stirred in the dark at RT for 18 h. The reaction mixture was poured into water (15 mL), the organic phase was separated and the water layer was extracted with ethyl acetate (3×10 mL). The combined organic extracts were washed with water and brine, dried over anhydrous Na$_2$SO$_4$ and filtered. The solvent was evaporated under vacuum at 40° C. The crude product was purified by "flash" column chromatography, using heptane/ethyl acetate (95:5) as the eluent. Sulfone G6 was obtained as a solid, with the yield of 1.16 g (90%).

G5:
$^1$H NMR (CDCl$_3$, 500 MHz) δ 5.53 (m, 1H, Br—CH$_2$—CH=), 5.07 (m, 1H, —CH$_2$—CH=), 4.03 (d, 2H, Br—CH$_2$—), 2.12-2.04 (m, 4H, —CH$_2$—CH$_2$—), 1.73 (d, 3H, —CH$_3$), 1.68 (d, 3H, —CH$_3$), 1.60 (s, 3H, —CH$_3$);
$^{13}$C NMR (CDCl$_3$, 125 MHz) δ 143.6, 132.0, 123.5, 120.5, 39.5, 29.7, 26.2, 25.7, 17.7, 16.0

G6:
$^1$H NMR (CDCl$_3$, 500 MHz) δ 7.88-7.86 (m, 2H, Ar), 7.66-7.62 (m, 1H, Ar), 7.56-7.51 (m, 2H, Ar), 5.20-5.17 (m, 1H, RO$_2$S—CH$_2$—CH=), 5.04-5.02 (m, 1H, —CH$_2$—CH=), 3.81 (d, 2H, RO$_2$S—CH$_2$—CH=), 2.05-1.98 (m, 4H—CH$_2$—CH$_2$—), 1.69 (s, 3H, —CH$_3$), 1.59 (d, 3H, —CH$_3$), 1.31 (d, 3H, —CH$_3$);
$^{13}$C NMR (CDCl$_3$, 125 MHz) δ 146.3, 138.6, 133.5, 132.0, 128.9, 128.5, 123.4, 110.2, 56.0, 39.6, 26.1, 25.6, 17.6, 16.1.

Example 3

(2E,6E)-8-Bromo-3,7-dimethylocta-2,6-dien-1-yl acetate (G3)

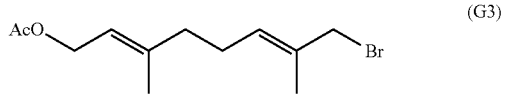
(G3)

PBr$_3$ (0.42 mL, 1.22 g, 4.5 mmol) was added dropwise at 0° C. to the solution of (2E,6E)-8-hydroxy-3,7-dimethyl-octa-2,6-dien-1-yl acetate G2 (2 g, 9.39 mmol) in anhydrous THF, and the resulting mixture was stirred at 0° C. for 2 h. The reaction was quenched by adding iced water. The organic layer was separated, and the water phase was extracted with diethyl ether (3×10 mL). The combined organic extracts were washed with saturated NaHCO$_3$ aq. solution and brine, dried over anhydrous Na$_2$SO$_4$, filtered and evaporated under vacuum to give (2E,6E)-8-bromo-3,7-dimethylocta-2,6-dien-1-yl acetate G3 as colorless oil (2.2 g, 8.03 mmol, 85%).

$^1$H NMR (CDCl$_3$, 500 MHz) δ 5.58-5.55 (m, 1H, —CH=CH$_2$—), 5.38-5.33 (m, 1H, —CH=CH$_2$—), 4.58 (d, 2H, —O—CH$_2$—CH=), 3.97 (s, 2H, CH$_2$—Br), 2.20-2.07 (m, 4H, —CH$_2$—CH$_2$—), 2.06 (s, 3H, CH$_3$—COOR), 1.76 (s, 3H, —CH$_3$), 1.70 (s, 3H, —CH$_3$);
$^{13}$C NMR (CDCl$_3$, 125 MHz) δ 171.1, 141.3, 132.4, 130.4, 118.8, 61.2, 41.6, 38.5, 26.3, 21.0, 16.4, 14.7

Example 4

Sulfone (G8)

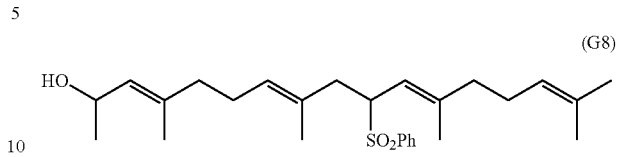
(G8)

(E)-1-((3,7-Dimethylocta-2,6-dien-1-yl)sulfonyl)-4-benzene G6 (3.5 g, 12.6 mmol) was dissolved in the mixture of anhydrous THF/DMF (50 mL, 4:1). The solution was cooled down to −78° C. (dry ice/MeOH) and t-BuOK (1.594 g, 14.2 mmol) in anhydrous THF was added dropwise (10 min.). The resulting yellow mixture was stirred at −78° C. for 2.5 h, then compound G3 (3.45 g, 12.6 mmol) in anhydrous THF was added. Stirring was continued at the same temperature for 4-5 h and the solution was left overnight to warm up to RT. The mixture was poured into the saturated NH$_4$Cl solution (100 mL). The organic phase was separated and the water layer was extracted with diethyl ether (3×10 mL). The combined organic extracts were washed with brine, dried over anhydrous Na$_2$SO$_4$, filtered and evaporated under reduced pressure. The crude product was dissolved in methanol (20 mL), 1M NaOH aq. solution was added to reach pH 12 and the mixture was stirred at RT for 1 h. After evaporation on vacuo, the residue was poured into water and the product was extracted with diethyl ether (3×100 mL). The resulting compound was isolated from the post-reaction mixture by column chromatography, using heptane/ethyl acetate (7:2). Oily product G8 was obtained with the yield of 2.7 g (6.28 mmol, 50%).

$^1$H NMR (CDCl$_3$, 500 MHz) δ 7.86-7.83 (m, 2H, Ar), 7.64-7.60 (m, 1H, Ar), 7.53-7.49 (m, 2H, Ar), 5.38 (t, 1H, —CH$_2$—CH=), 5.15 (t, 1H, —CH$_2$—CH=), 5.02 (m, 1H, —CH$_2$—CH=), 4.9 (d, 1H, —CH$_2$—CH=), 4.15-4.12 (d, 2H, HO—CH$_2$—), 3.90-3.85 (m, 1H, RO$_2$S—CH—), 2.90-2.86 (dd, 1H, RO$_2$S—CH—CH$_2$), 2.31-2.26 (m, 1H, RO$_2$S—CH—CH$_2$), 2.08-2.02 (m, 2H, —CH$_2$—), 1.99-1.92 (m, 6H, —CH$_2$—), 1.68 (s, 3H, —CH$_3$), 1.64 (s, 3H, —CH$_3$), 1.58 (s, 3H, —CH$_3$), 1.53 (s, 3H, —CH$_3$), 1.16 (d, 3H, —CH$_3$);
$^{13}$C NMR (CDCl$_3$, 125 MHz) δ 144.9, 139.3, 137.9, 133.3, 131.9, 130.2, 129.22, 129.17, 128.7, 127.8, 123.5, 123.4, 117.2, 63.4, 59.3, 39.6, 39.2, 37.4, 26.29, 26.26, 25.7, 17.64, 16.3, 16.2, 15.9;
LC-MS (ESI) calc. for C$_{26}$H$_{38}$O$_3$S (M+H)$^+$: 430.6, found: 430.5.

Example 5

Disulfone (G10)

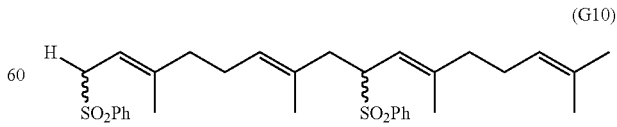
(G10)

PBr$_3$ (0.11 mL, 0.31 g, 1.1 mmol) was added dropwise at 0° C. to the solution of sulfone G8 (1 g, 2.33 mmol) in anhydrous THF, and the resulting mixture was stirred at 0° C. for 3 h. The reaction was quenched by adding iced water.

The organic layer was separated, and the water phase was extracted with diethyl ether (3×10 mL). The combined organic extracts were washed with saturated NaHCO$_3$ aq. solution and brine, dried over anhydrous Na$_2$SO$_4$, filtered and evaporated under vacuum to give a crude bromide compound as colorless oil (1.1 g, 2.24 mmol, 87%). The crude bromide was dissolved in anhydrous DMF (5 mL) and PhSO$_2$Na (1 g, 6.1 mmol) was added. The solution was stirred in the dark at RT for 18 h. The reaction mixture was poured into water (15 mL), the organic phase was separated, the water layer was extracted with ethyl acetate (3×10 mL). The combined organic extracts were washed with water and brine, dried over anhydrous Na$_2$SO$_4$ and filtered. The solvent was evaporated under vacuum at 40° C. The crude product was purified by "flash" column chromatography, using heptane/ethyl acetate (95:5) as the eluent. Sulfone G10 was obtained as a solid, with the yield of 1.23 g (79%).

$^1$H NMR (CDCl$_3$, 500 MHz) δ 7.87-7.82 (m, 4H, Ar), 7.65-7.59 (m, 2H, Ar), 7.55-7.48 (m, 4H, Ar), 5.15 (t, 1H, RO$_2$S—CH$_2$—CH=), 5.07 (m, 1H, —CH2-CH=), 5.01 (m, 1H, —CH$_2$—CH=), 4.89 (d, 1H, —CH2-CH=), 3.90-3.83 (m, 1H, RO$_2$S—CH—), 3.80-3.78 (m, 2H, RO$_2$S—CH$_2$—), 2.90-2.86 (d, 1H, RO$_2$S—CH—CH$_2$), 2.30-2.24 (m, 1H, RO$_2$S—CH—CH$_2$), 2.00-1.88 (m, 8H, —CH$_2$—), 1.67 (s, 3H, —CH$_3$), 1.58 (s, 3H, —CH$_3$), 1.50 (s, 3H, —CH$_3$), 1.29 (s, 3H, —CH$_3$), 1.15 (d, 3H, —CH$_3$);

$^{13}$C NMR (CDCl$_3$, 125 MHz) δ 146.0, 145.0, 138.6, 137.8, 133.6, 133.4, 131.9, 130.6, 129.2, 129.0, 128.7, 128.4, 127.3, 123.5, 117.2, 110.4, 63.4, 56.0, 39.6, 39.3, 37.3, 26.3, 26.2, 25.7, 17.65, 16.3, 16.1, 15.9.

Example 6

Hydroxy-disulfone (G12)

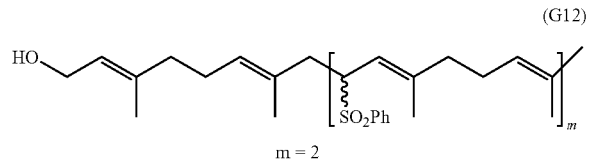

Sulfone G10 (7.1 g, 12.8 mmol) was dissolved in the mixture of anhydrous THF/DMF (50 mL, 4:1). The solution was cooled down to −78° C. (dry ice/MeOH) and t-BuOK (1.594 g, 14.2 mmol) in anhydrous THF was added dropwise (10 min.). The resulting yellow mixture was stirred at −78° C. for 2.5 h, then compound G3 (3.5 g, 12.8 mmol) in anhydrous THF was added. Stirring was continued at the same temperature for 4-5 h and the solution was left overnight to warm up to RT. The mixture was poured into the saturated NH$_4$Cl solution (100 mL). The organic phase was separated and the water layer was extracted with ether (3×10mL). The combined organic extracts were washed with brine, dried over anhydrous Na$_2$SO$_4$, filtered and evaporated under reduced pressure. The crude product was dissolved in methanol (20 mL), 1M NaOH aqueous solution was added to reach pH 12 and the mixture was stirred at RT for 1 h. After evaporation on vacuo, the residue was poured into water and the product was extracted with diethyl ether (3×100 mL). The resulting compound G12 was separated from the crude mixture by column chromatography, using heptane/ethyl acetate (7:2). The oily product G12 was obtained with the yield of 4.52 g (6.4 mmol, 50%).

$^1$H NMR (CDCl$_3$, 500 MHz) δ 7.84-7.82 (m, 4H, Ar), 7.63-7.59 (m, 2H, Ar), 7.52-7.49 (m, 4H, Ar), 5.38-5.33 (m, 1H, —CH=CH$_2$—), 5.15 (t, 1H, RO$_2$S—CH$_2$—CH=), 5.08 (m, 1H, —CH$_2$—CH=), 5.02 (m, 1H, —CH$_2$—CH=), 4.90-4.87 (m, 2H, —CH$_2$—CH=), 4.14-4.10 (m, 2H, —O—CH$_2$—CH=), 3.90-3.83 (m, 2H, RO$_2$S—CH—), 2.90-2.82 (t, 2H, RO$_2$S—CH—CH$_2$), 2.30-2.24 (m, 2H, RO$_2$S—CH—CH$_2$), 2.10-1.83 (m, 13H), 1.68 (s, 3H, —CH$_3$), 1.64 (s, 3H, —CH$_3$), 1.58 (s, 3H, —CH$_3$), 1.52 (s, 3H, —CH$_3$), 1.50 (s, 3H, —CH$_3$), 1.26 (m, 1H), 1.14 (m, 6H, —CH$_3$);

$^{13}$C NMR (CDCl$_3$, 125 MHz) δ 145.0, 144.6, 139.0, 137.9, 137.8, 133.4, 131.9, 130.5, 130.4, 130.1, 129.2, 129.1, 128.7, 127.8, 127.5, 127.4, 123.5, 117.3, 117.2, 63.3, 59.2, 39.6, 39.3, 39.1, 37.4, 37.3, 26.4, 26.3, 26.2, 25.6, 17.6, 16.3, 16.2, 15.9, 15.8, 15.7. LC-MS (ESI) calc. for C$_{42}$H$_{58}$O$_5$S$_2$(M+H)$^+$: 707.04, found: 707.0.

Example 7

Hexaprenyl Bromide (G13)

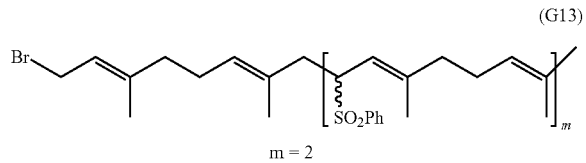

PBr$_3$ (0.42 mL, 1.22 g, 4.5 mmol) was added dropwise at 0° C. to the solution of G12 (6.35 g, 9 mmol) in anhydrous THF. The resulting mixture was stirred at 0° C. for 3 h. The reaction was quenched by adding iced water. The organic layer was separated, the water phase was extracted with ether (3×10 mL). The combined organic extracts were washed with a saturated aqueous NaHCO$_3$ solution and brine, dried over anhydrous Na$_2$SO$_4$, filtered and evaporated under vacuum to give bromide G13 as colorless oil (6.21 g, 8.09 mmol, 90%).

Example 8

Diallyl-menadiol (12)

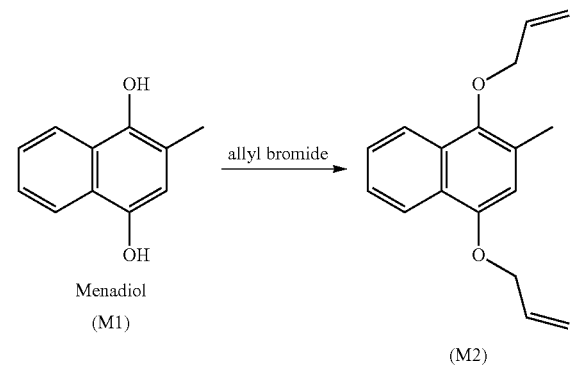

K$_2$CO$_3$ (61.8 g, 446.9 mM), 18-Crown-6 ether (0.1 g) and allyl bromide (11.7 mL, 132.2 mM) were added to the solution of menadiol (9.73 g, 55.9 mM) in acetone (195 mL). The suspension was stirred for 24 h at RT. K$_2$CO$_3$ was filtered off and the filtrate was concentrated under the reduced pressure. The residue was dissolved in DCM (300 mL), and washed with water (150 mL). The organic phase was concentrated and purified by column chromatography (hexane/ethyl acetate 95:5→90:10) to obtain an oily product M2 (11.45 g, 82%).

$^1$H NMR (CDCl$_3$, 500 MHz) δ 8.25 (d, J=5 Hz, 1H), 8.01 (d, J=5 Hz, 1H), 7.51-7.48 (m, 1H), 7.44-7.40 (m, 1H), 6.62 (s, 1H), 6.23-6.14 (m, 2H, —CH=CH$_2$), 5.53-5.48 (m, 2H, —CH=CH$_2$), 5.34-5.29 (m, 2H, —CH=CH$_2$), 4.68-4.67 (m, 2H, —O—CH$_2$—CH=CH$_2$), 4.45-4.44 (m, 2H, —O—CH$_2$—CH=CH$_2$), 2.43 (s, 3H, CH$_3$).

$^{13}$C NMR (CDCl$_3$, 125 MHz) δ 150.4, 145.9, 134.2, 133.4, 128.9, 126.4, 125.8, 125.3, 124.5, 122.3, 121.5, 117.3, 117.2. 108.1, 74.5, 69.1, 16.5.

HR-MS (ESI) calc. for C$_{17}$H$_{18}$O$_2$ (M+H)$^+$: 254.1307. Found: 254.1312.

Example 9

Phenylsulfone of monoprenyl-menadiol (MG1)

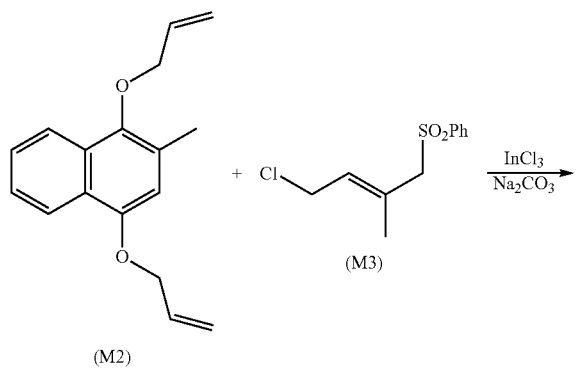

A mixture of M2 (7.3 g, 28.62 mM), (E)-4-chloro-2-methyl-1-phenylsulfonyl-2-butene (9.1 g, 37.2 mM), and Na$_2$CO$_3$ (7.6 g, 71.55 mM) in DCM (150 mL) was cooled to 0° C. InCl$_3$ (6.33, 28.62 mM) was added and the reaction was stirred at RT for 6 h. Then, water (50 mL) was added, the organic phase was separated and evaporated to give the brown oil. The crude product was purified by column chromatography (hexane/ethyl acetate 5:1→3:1) to obtain an oily product M4 (7.2 g, 54%).

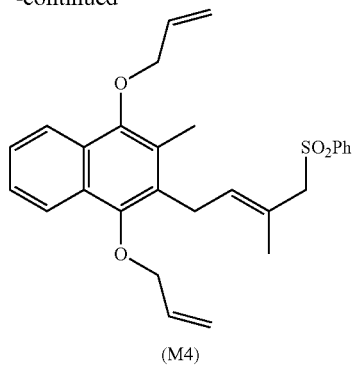

$^1$H NMR (CDCl$_3$, 500 MHz) δ 8.05 (d, J=5 Hz, 1H), 7.97 (d, J=5 Hz, 1H), 7.74-7.72 (m, 2H), 7.46-7.45 (m, 2H), 7.30-7.26 (m, 3H), 6.20-6.15 (m, 2H, —CH=CH$_2$), 5.54-5.50 (m, 2H, —CH=CH$_2$), 5.34-5.29 (m, 2H, —CH=CH$_2$), 5.01 (t, 1H), 4.69-4.68 (m, 2H, —O—CH$_2$—CH=CH$_2$), 4.42-4.41 (m, 2H, —O—CH$_2$—CH=CH$_2$), 3.49-3.47 (m, 2H), 2.21 (s, 3H), 2.04 (s, 3H), 1.98 (br s, 2H).

$^{13}$C NMR (CDCl$_3$, 125 MHz) δ 149.0, 148.6, 138.0, 134.2. 133.9, 133.8, 133.3, 129.3, 128.9, 128.5, 128.2, 127.8, 125.7, 125.4, 123.9, 122.2, 122.1, 117.3, 117.2, 75.2, 74.5, 65.9, 30.9, 26.8, 17.1, 16.8, 12.7.

HR-MS (ESI) calc. for C$_{28}$H$_{30}$O$_4$SNa (M+Na)$^+$: 485.1762. Found: 485.1765.

Example 10

Triphenylsulfonyl-heptaprenyl diallyl-menadiol (MG1)

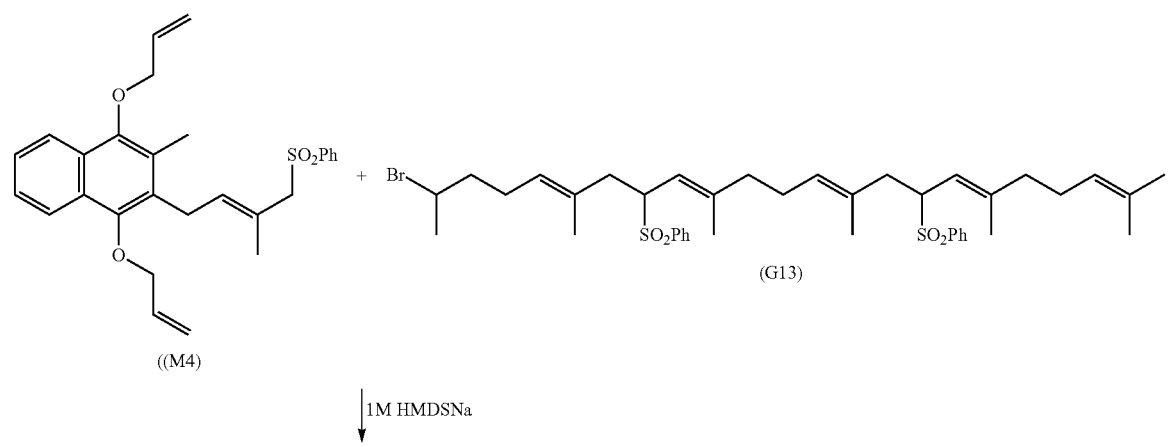

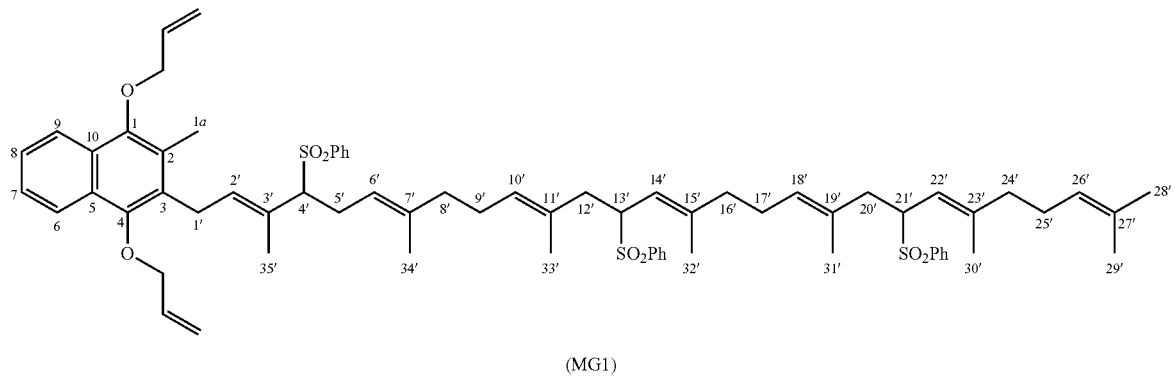

(MG1)

The solution of M4 (84 mg, 0.182 mM) and G13 (200.0 mg, 0.259 mM) in THF (5 mL) and DMF (0.4 mL) under the nitrogen atmosphere was cooled to −20° C. Then, 1M HMDSNa in THF (0.45 mL) was added dropwise and stirring was continued at −20° C. until completion of the reaction (TLC). After 2 h, the reaction was quenched with $H_2O$ and the crude product was extracted with AcOEt (3×10 mL). The organic extracts were combined, washed with brine, and dried over anhydrous $MgSO_4$. The drying agent was filtered off and the residue was evaporated to give the oil. The column chromatography (hexane/ethyl acetate 10:1→3:1) of the residue gave the oily product MG1 (188 mg, 90%).

$^1$H NMR (CDCl$_3$, 500 MHz) δ 8.02-8.01 (m, 1H, H-9), 7.97-7.96 (m, 1H, H-6), 7.83-7.81 (m, 6H, SO$_2$Ph), 7.61-7.60 (m, 3H, SO$_2$Ph), 7.54-7.48 (m, 6H, SO$_2$Ph), 7.45 (m, 1H, H-8), 7.40 (m, 1H, H-7), 6.18-6.15 (m, 2H, —CH=CH$_2$), 5.51-5.49 (m, 2H, —CH=CH$_2$), 5.32-5.30 (m, 2H, —CH=CH$_2$), 5.10-5.01 (m, 4H, H-2', H-10', H-18', H-26'), 4.87-4.86 (m, 3H, H-6', H-14', H-22'), 4.40-4.39 (m, 2H, —O—CH$_2$—CH=CH$_2$), 4.32-4.31 (m, 2H, —O—CH$_2$—CH=CH$_2$), 3.85-3.84 (m, 2H, H-13', H-21'), 3.47-3.46 (m, 2H, H-1'), 3.46-3.45 (m, 1H, H-4'), 2.86-2.81 (m, 3H, H-5', H-12', H-20'), 2.60-2.61 (m, 1H, H-5'), 2.26-2.23 (m, 2H, H-12', H-20'), 2.14 (s, 3H, H-1a), 2.02-2.01 (m, 6H, H-9', H-17', H-25'), 2.00-1.98 (m, 6H, H-8', H-16', H-24'), 1.67 (s, 3H, CH$_3$-28'), 1.80-1.58 (m, 21H, CH$_3$-35', CH$_3$-34', CH$_3$-33', CH$_3$-32', CH$_3$-31', CH$_3$-30', CH$_3$-29').

$^{13}$C NMR (CDCl$_3$, 125 MHz) δ 149.0 (C-1), 148.6 (C-4), 145.0 (C-15'), 144.7 (C-23'), 138.2 (C-7'), 137.9 (SO$_2$Ph), 137.8 (SO$_2$Ph), 137.6 (SO$_2$Ph), 134.0 (C-2'), 133.95 (—CH=CH$_2$), 133.91 (—CH=CH$_2$), 133.8-133.2 (SO$_2$Ph), 131.9 (C-27'), 130.5 (C-11'), 130.0 (C-19'), 129.3 (C-3), 128.7-128.5 (SO$_2$Ph), 127.5 (C-5, C-10), 127.8-127.4 (C-10', C-18'), 126.6 (C-2), 125.6 (C-8), 125.4 (C-7), 123.5 (C-26'), 122.2 (C-6), 122.1 (C-9), 118.79 (C-6'), 117.3-117.0 (—CH=CH$_2$, C-14', C-22'), 75.1 (—O—CH$_2$—CH=CH$_2$), 74.5 (—O—CH$_2$—CH=CH$_2$), 73.7 (C-4'), 63.4-63.3 (C-13', C-21'), 39.6-38.5 (C-8', C-16', C-24'), 37.3-37.0 (C-12', C-20'), 26.6-26.2 (C-1', C-9', C-17', C-25'), 25.6 (C-28'), 23.9 (C-5'), 17.6-14.0 (C-35', C-34', C-33', C-32', C-31', C-30', C-29'), 12.6 (C-1a). HR-MS (ESI) calc. for C$_{70}$H$_{86}$O$_8$S$_3$Na (M+Na)$^+$: 1173.5392. Found: 1173.5383.

Example 11

Phenylsulfonyl-heptaprenyl diallyl-menadiol (MG11)

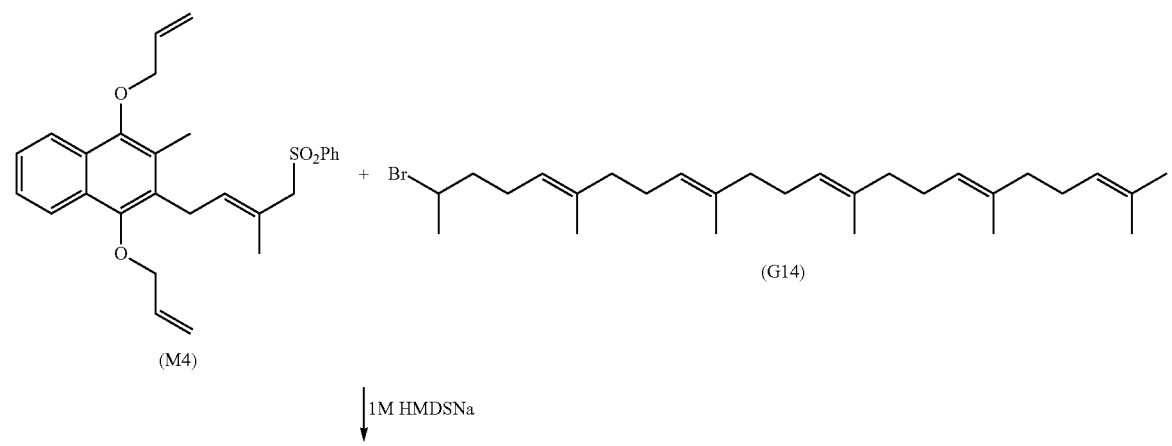

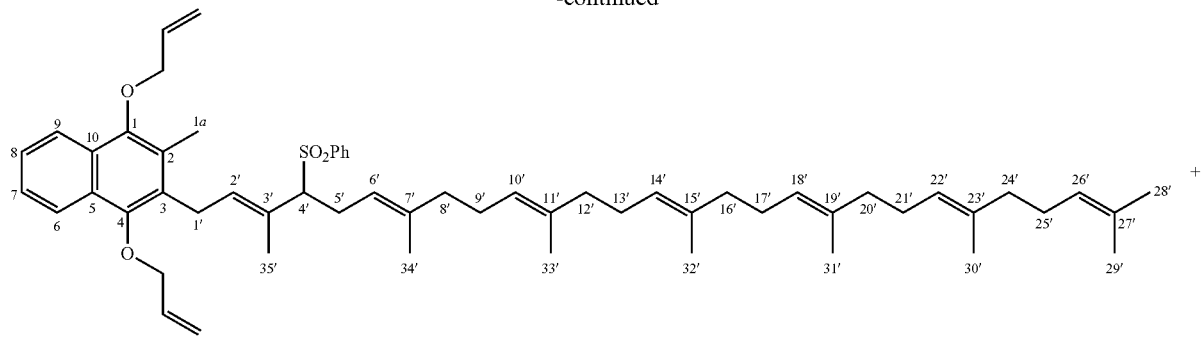

(MG11)

The solution of M4 (190.0 mg, 0.41 mM) and hexaprenyl bromide G14 (281.0 g, 0.58 mM) in THF (6 mL) and DMF (0.6 mL) under nitrogen atmosphere was cooled to −20° C. Then, 1M HMDSNa in THF (1.23 mL) was added dropwise and stirring was continued at −20° C. until completion of the reaction (TLC). After 2 h, the reaction was quenched with $H_2O$ and the crude product was extracted with AcOEt (3×10 mL). The organic extracts were combined, washed with brine, and dried over anhydrous $MgSO_4$. The drying agent was filtered off and the residue was evaporated to give the oil. The column chromatography (hexane/ethyl acetate 10:1→5:1) of the residue gave the oily product MG11 (210 mg, 59%).

$R_f$=0.55 (hexane/ethyl acetate 5:1).

$^1H$ NMR ($CDCl_3$, 500 MHz) δ 8.04-8.02 (m, 1H, H-9), 7.99-7.98 (m, 1H, H-6), 7.74-7.73 (m, 2H, $SO_2Ph$), 7.45-7.44 (m, 2H, H-8, H-7), 7.38-7.26 (m, 3H, $SO_2Ph$), 6.18-6.15 (m, 2H, —CH=$CH_2$), 5.54-5.52 (m, 2H, —CH=$CH_2$), 5.34-5.31 (m, 2H, —CH=$CH_2$), 5.11-5.04 (m 6H, H-2', H-10', H-14', H-18', H-22', H-26'), 4.88 (m, 1H, H-6'), 4.40-4.39 (m, 2H, —O—$CH_2$—CH=$CH_2$), 4.32-4.31 (m, 2H, —O—$CH_2$—CH=$CH_2$), 3.48-3.47 (m, 2H, H-1', H-4'), 3.41-3.40 (m, 1H, H-1'), 2.81-2.80 (m, 1H, H-5'), 2.62-2.61 (m, 1H, H-5'), 2.16 (s, 3H, H-1a), 2.06-2.00 (m, 20H, H-8', H-9', H-12', H-13', H-16', H-17', H-20', H-21', H-24', H-25'), 1.88 (s, 3H, H-35'), 1.68 (s, 3H, H-28'), 1.59-1.53 (m, 18H, H-34', H-33', H-32', H-31', H-30', H-29').

$^{13}C$ NMR ($CDCl_3$, 125 MHz) δ 149.0 (C-1), 148.6 (C-4), 138.6 (C-7'), 137.7 ($SO_2Ph$), 135.3-134.8 (C-11', C-15', C-19', C-23'), 134.1 (C-2'), 133.95 (—CH=$CH_2$), 133.91 (—CH=$CH_2$), 133.18 ($SO_2Ph$), 131.2 (C-27'), 129.1 (C-3), 128.6-128.3 (SO2Ph), 127.8 (C-10), 127.4 (C-3'), 127.3 (C-5), 126.5 (C-2), 125.6 (C-8), 125.4 (C-7), 124.3 (C-26'), 124.4-123.2 (C-10', C-14', C-18', C-22'), 122.2 (C-6), 122.1 (C-9), 118.4 (C-6'), 117.3-117.0 (—CH=$CH_2$), 75.1 (—O—$CH_2$—CH=$CH_2$), 74.5 (—O—$CH_2$—CH=$CH_2$), 73.8 (C-4'), 39.7-39.6 (C-8', C-12', C-16', C-20', C-24'), 26.6-25.6 (C-1', C-9', C-13', C-17', C-21', C-25'), 25.6 (C-28'), 17.6 (C-29'), 16.3-15.9 (C-34', C-33', C-32', C-31', C-30'), 14.1 (C-35'), 12.6 (C-1a).

HR-MS (ESI) calc. for $C_{58}H_{78}O_4S$ $(M+H)^+$: 871.5699. Found: 871.5673.

Impurity (Imp. 1)

As the by-product, the impurity 16 was isolated by column chromatography from the crude oil, resulting from the alkylation of M4 with the hexaprenyl bromide. The impurity Imp. (1) was obtained as an oil (80 mg, 22%). The structure has been identified as:

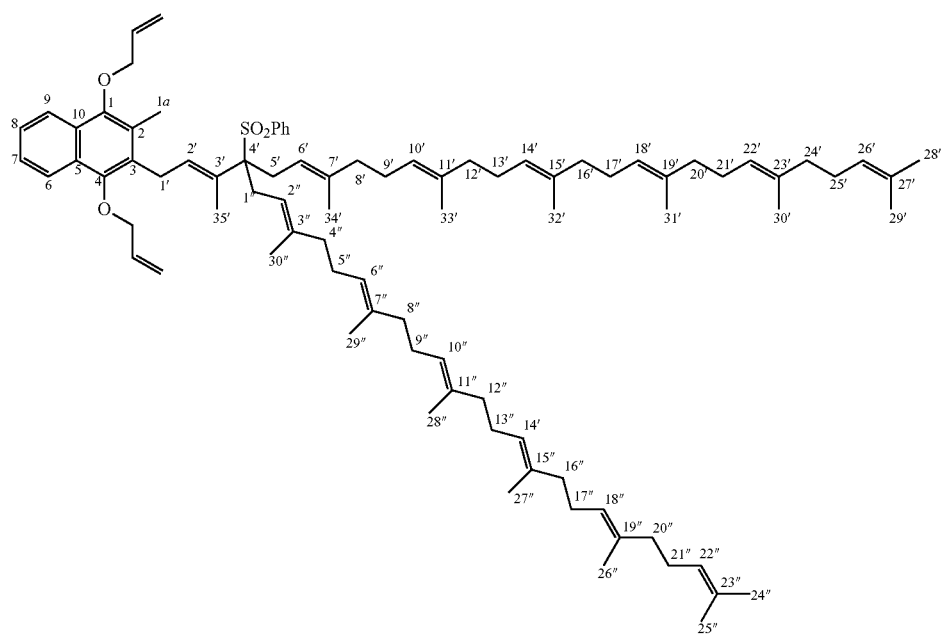

Imp. (1)

$R_f$=0.67 (hexane/ethyl acetate 5:1)

$^1$H NMR (CDCl$_3$, 500 MHz) δ 8.03-7.98 (m, 2H, H-6, H-9), 7.71-7.69 (m, 2H, SO$_2$Ph), 7.45-7.44 (m, 3H, H-8, H-7, SO$_2$Ph), 7.30-7.26 (m, 2H, SO$_2$Ph), 6.18-6.15 (m, 2H, —CH=CH$_2$), 5.55-5.51 (m, 2H, —CH=CH$_2$), 5.34-5.30 (m, 2H, —CH=CH$_2$), 5.11-5.09 (m, 13H, H-2', H-6', H-10', H-14', H-18', H-22', H-26', H-2", H-6", H-10", H-14", H-18", H-22"), 4.40-4.39 (m, 2H, —O—CH$_2$—CH=CH$_2$), 4.35-4.34 (m, 2H, —O—CH$_2$—CH=CH$_2$), 3.52-3.51 (m, 2H, H-1'), 2.74-2.64 (m, 4H, H-5', H-1"), 2.18 (s, 3H, H-1a), 2.06-1.96 (m, 40H, H-8', H-9', H-12', H-13', H-16', H-17', H-20', H-21', H-24', H-25', H-4", H-5", H-8", H-9", H-12", H-13", H-16", H-17", H-20", H-21"), 1.96 (s, 314, H-35'), 1.68 (s, 3H, H-28'), 1.60 (s, 3H, H-29'), 1.62-1.51 (m, 36H, H-34', H-33', H-32', H-31', H-30', H-24", H-25", H-26", H-27", H-28", H-29", H-30").

$^{13}$C NMR (CDCl$_3$, 125 MHz) δ 149.0 (C-1), 148.6 (C-4), 137.4 (C-7', C-3"), 135.7-135.0 (SO$_2$Ph, C-11', C-15', C-19', C-23', C-7", C-11", C-15", C-19", C-23"), 133.9-133.8 (—CH=CH$_2$), 133.4-133.0 (SO$_2$Ph, C-2'), 131.2 (C-27'), 131.1 (C-3'), 130.2 (SO$_2$Ph), 129.4 (C-3), 128.1 (SO$_2$Ph), 127.7 (C-10), 127.3 (C-5), 126.6 (C-2), 125.6 (C-8), 125.5 (C-7), 124.4-124.1 (C-10', C-14', C-18', C-22', C-26', C-6", C-10", C-14", C-18", C-22"), 122.2 (C-9), 122.1 (C-6), 118.1 (C-6'), 117.2 (—CH=CH$_2$), 117.0 (—CH=CH$_2$), 75.1-74.5 (—O—CH$_2$—CH=CH$_2$), 73.7 (C-4'), 39.0 (C-8', C-12', C-16', C-20', C-24', C-4", C-8", C-12", C-16", C-20"), 29.6 (C-5'), 27.2 (C-1'), 25.6 (C-28', C-24"), 26.9-26.3 (C-9', C-13', C-17', C-21', C-25', C-5", C-9", C-13", C-17", C-21"), 17.6 (C-29'), 16.4 (C-34'), 15.0 (C-35'), 16.0-15.8 (C-33', C-32', C-31', C-30', C-30", C-29", C-28", C-27", C-26", C-25"), 12.8 (C-1a).

HR-MS (ESI) calc. for C$_{88}$H$_{130}$NO$_4$S (M+NH$_4$)$^+$: 1296.9721. Found: 1296.9717.

Example 13

Heptaprenyl diallyl-menadiol (MG2)

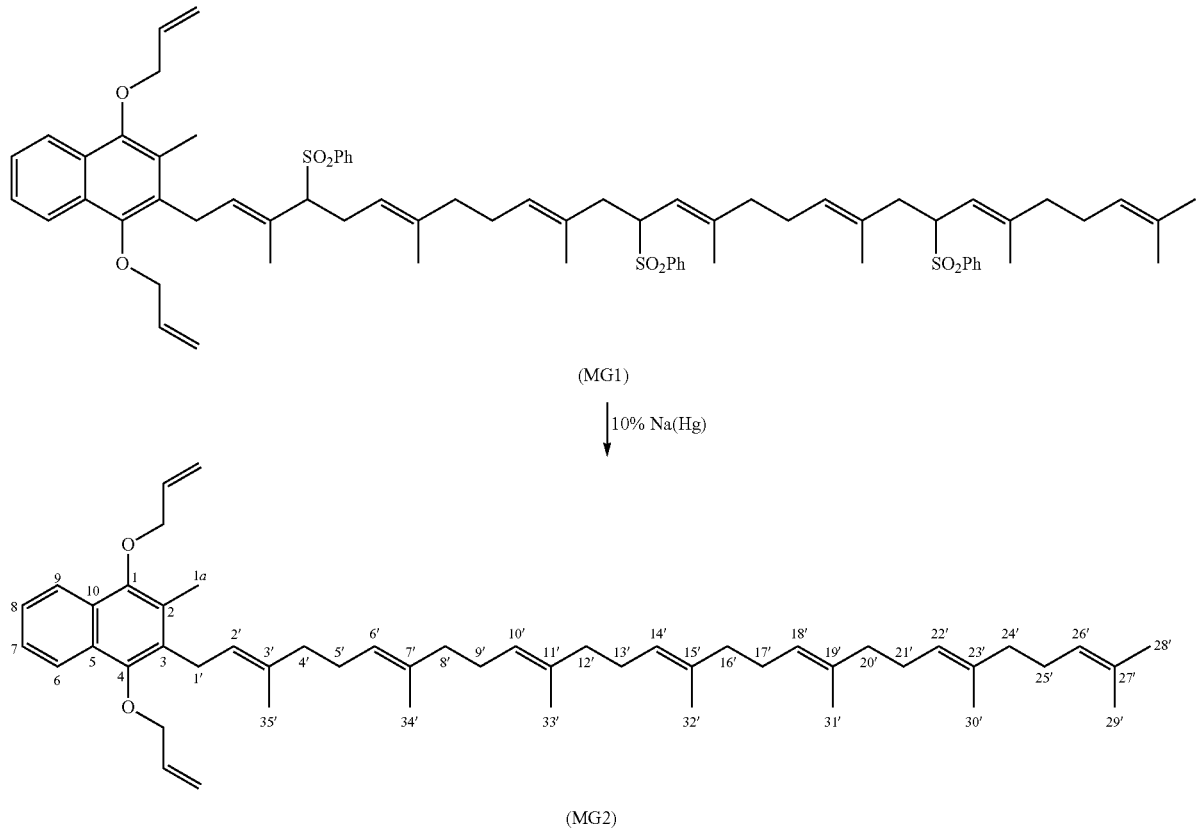

The solution of MG1 (50 mg, 0.043 mM) in dry THF (3 mL) was stirred under argon atmosphere at RT. Then, the solution of Na$_2$HPO$_4$ (3 mL) and the first portion of 10% Na(Hg) (50 mg) were added to the mixture. The second portion of 10% Na(Hg) (50 mg) was added after 1 h, and the last portion of 10% Na(Hg) (50 mg) was added after further 1 h. The reaction was stirred for subsequent 5 h. Then, water (10 mL) and AcOEt (10 mL) were added, the organic phase was separated, washed with brine and evaporated to give the brown oil. The crude product was purified by column chromatography (hexane/ethyl acetate 20:1) to obtain an oily product MG2 (27 mg, 85%).

$^1$H NMR (CDCl$_3$, 500 MHz) δ 8.04-8.03 (m, 2H, H-6, H-9), 7.45-7.43 (m, 2H, H-8, H-7), 6.21-6.20 (m, 2H, —CH=CH$_2$), 5.55-5.51 (m, 2H, —CH=CH$_2$), 5.33-5.31 (m, 2H, —CH=CH$_2$), 5.11-5.10 (m 7H, H-2', H-6', H-10', H-14', H-18', H-22', H-26'), 4.45-4.44 (m, 4H, —O—CH$_2$—CH=CH$_2$), 3.58-3.57 (m, 2H, H-1'), 2.38 (s, 3H, H-1a), 2.07-1.99 (m, 24H, H-4', H-5', H-8', H-9', H-12', H-13', H-16', H-17', H-20', H-21', H-24', H-25'), 1.81 (s, 3H, H-35'), 1.68 (s, 3H, H-28'), 1.65-1.54 (m, 18H, H-34', H-33', H-32', H-31', H-30', H-29').

$^{13}$C NMR (CDCl$_3$, 125 MHz) δ 148.9 (C-1), 148.5 (C-4), 135.8 (C-3'), 135.1-135.04 (C-7', C-11', C-15', C-19', C-23'), 134.9-134.8 (—CH=CH$_2$), 131.2 (C-27'), 131.08 (C-3), 127.6-127.1 (C-2, C-5, C-10), 125.5-125.2 (C-7, C-8), 124.3-124.1 (C-6', C-10', C-14', C-18', C-22', C-26'), 122.7 (C-2'), 122.2-122.1 (C-6, C-9), 117.1-117.0 (—CH=CH$_2$), 75.3-75.2 (—O—CH$_2$—CH=CH$_2$), 39.7 (C-4', C-8', C-12', C-16', C-20', C-24'), 26.7-26.4 (C-1', C-5', C-9', C-13', C-17', C-21', C-25'), 25.6 (C-28'), 17.6 (C-29'), 16.4 (C-35'), 16.0-15.9 (C-34', C-33', C-32', C-31', C-30'), 12.7 (C-1a).

HR-MS (ESI) calc. for C$_{52}$H$_{74}$O$_2$ (M+H)$^+$: 731.5767. Found: 731.5764.

Example 14

Heptaprenyl diallyl-menadiol (MG2)

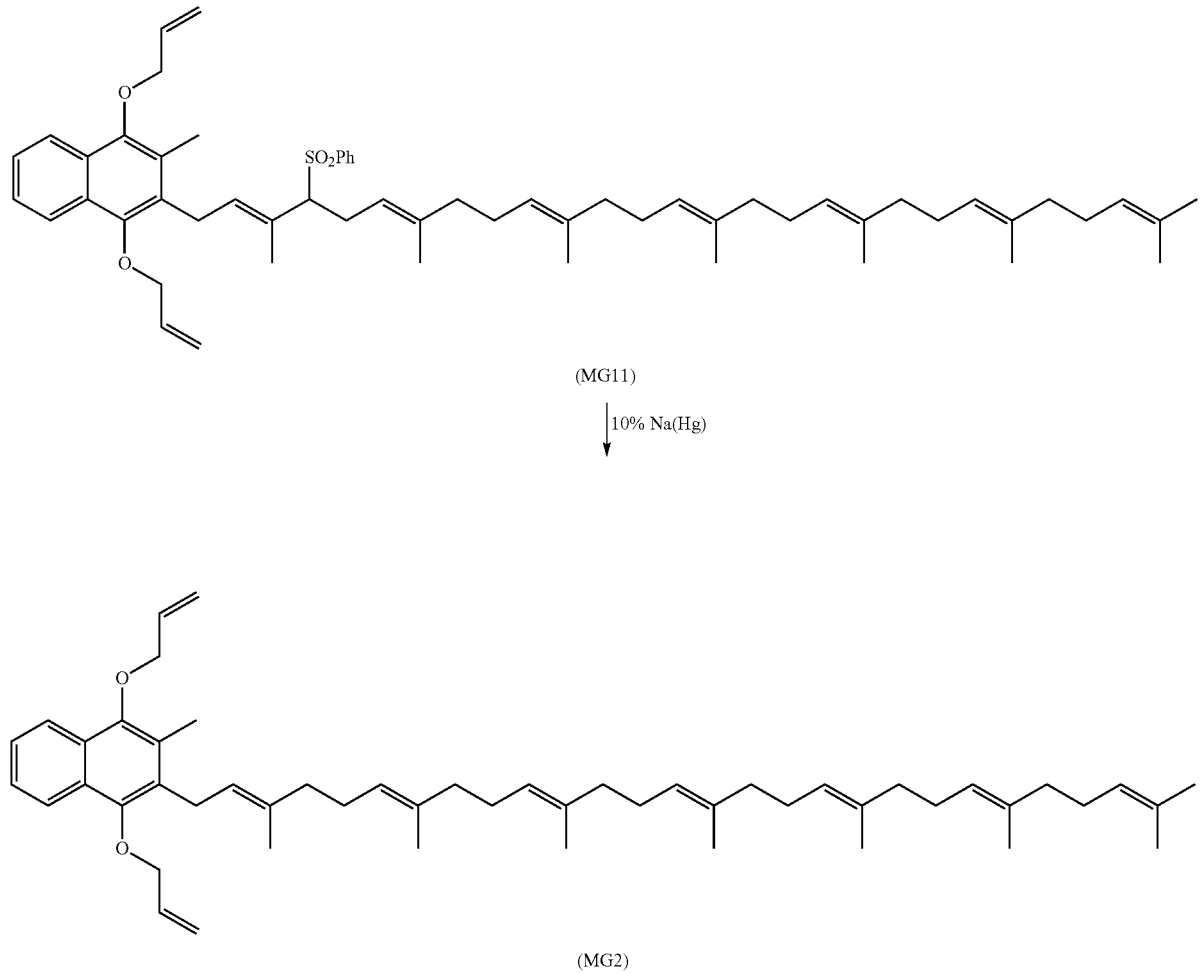

The solution of MG11 (178 mg, 0.2 mM) in dry THF (4 mL) was stirred under argon atmosphere at RT. Then, the solution of Na$_2$HPO$_4$ (4 mL) and the first portion of 10% Na(Hg) (70 mg) were added to the mixture. The second portion of 10% Na(Hg) (70 mg) was added after 1 h, and the reaction was stirred for subsequent 1 h. Then, water (8 mL) and AcOEt (15 mL) were added, the organic phase was separated, washed with brine and evaporated to give the brown oil. The crude product was purified by column chromatography (hexane/ethyl acetate 20:1) to obtain an oily product MG2 (140 mg, 94%). NMR consistent with Example 13 data.

Example 15

Vitamin MK-7

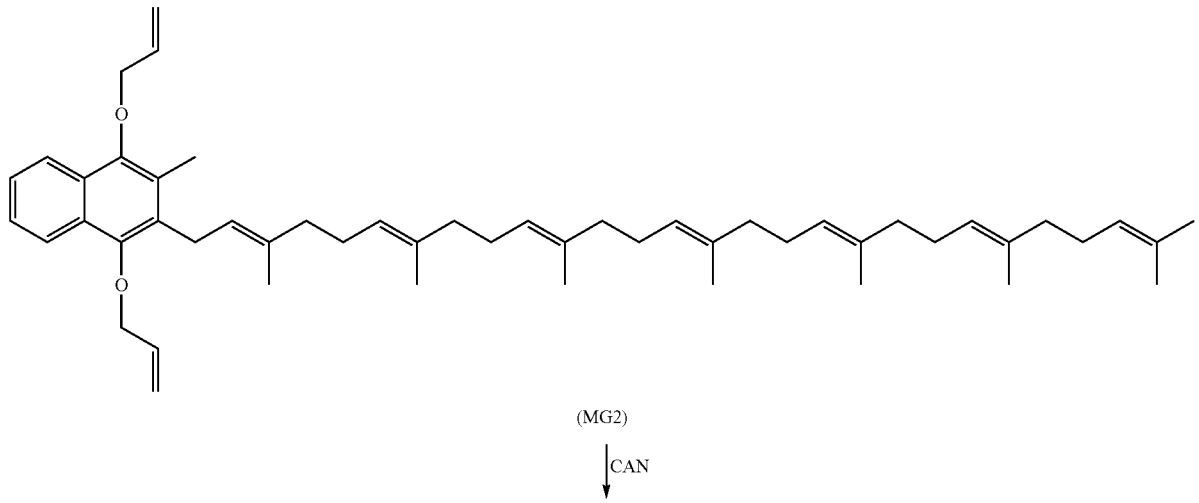

(MG2)

↓ CAN

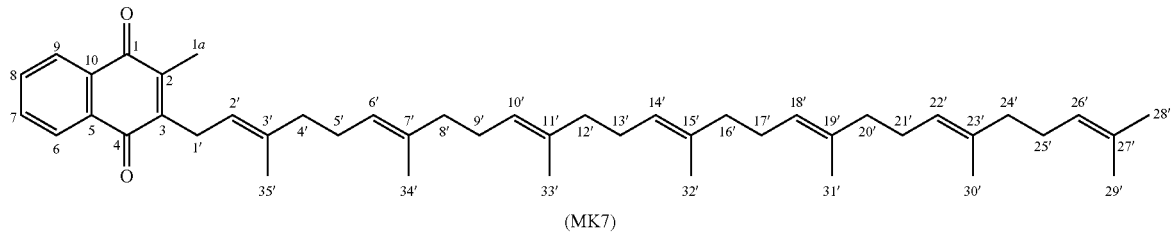

(MK7)

A solution of ammonium cerium (IV) nitrate (CAN) (376 mg, 0.685 mM) in acetonitrile (2 mL) and water (0.35 mL) was added to the solution of MG2 (200 mg, 0.274 mM) in the mixture of acetonitrile and DCM (1:1, 6 mL) at 0° C. The reaction was stirred for 1 h, then water (10 mL) was added and the solution was extracted with DCM (3×10 mL). The organic phase was washed with brine, water, and evaporated to give the yellow oil. The crude product was purified by column chromatography (hexane/ethyl acetate 20:1) to obtain an oily product MK-7 (142 mg, 79%). The oily product was crystallized in the mixture of ethyl acetate and ethanol, and vitamin MK-7 as the yellow solid was obtained with the yield of 98% (140 mg).

$^1$H NMR (CDCl$_3$, 500 MHz) δ 8.08-8.07 (m, 2H, H-6, H-9), 7.69-7.68 (m, 2H, H-8, H-7), 5.11-5.02 (m, 7H, H-2', H-6', H-10', H-14', H-18', H-22', 11-26'), 3.38-3.36 (m, 2H, H-1'), 2.19 (s, 3H, H-1a), 2.06-1.97 (m, 24H, H-4', H-5', H-8', H-9', H-12', H-13', H-16', H-17', H-20', H-21', H-24', H-25'), 1.79 (s, 3H, H-35'), 1.68 (s, 3H, H-28'), 1.59-1.56 (m, 18H, H-34', H-33', H-32', H-31', H-30', H-29').

$^{13}$C NMR (CDCl$_3$, 125 MHz) δ 185.4 (C-1), 184.5 (C-4), 146.1 (C-3), 143.3 (C-2), 137.5 (C-3'), 135.2-134.8 (C-7', C-11', C-15', C-19', C-23'), 133.3-133.2 (C-7, C-8), 132.2-132.1 (C-5, C-10), 131.2 (C-27'), 126.2-126.1 (C-8, C-9), 124.3-123.8 (C-6', C-10', C-14', C-18', C-22', C-26'), 119.0 (C-2'), 39.7 (C-4', C-8', C-12', C-16', C-20', C-24'), 26.7-26.4 (C-5', C-9', C-13', C-17', C-21', C-25'), 25.9 (C-1'), 25.6 (C-28'), 17.6 (C-29'), 16.4 (C-35'), 16.0 (C-34', C-33', C-32', C-31', C-30'), 12.6 (C-1a).

HR-MS (ESI) calc. for C$_{46}$H$_{64}$O$_2$Na (M+H)$^+$: 671.4804. Found: 671.4797.

Example 16

Vitamin MK-7

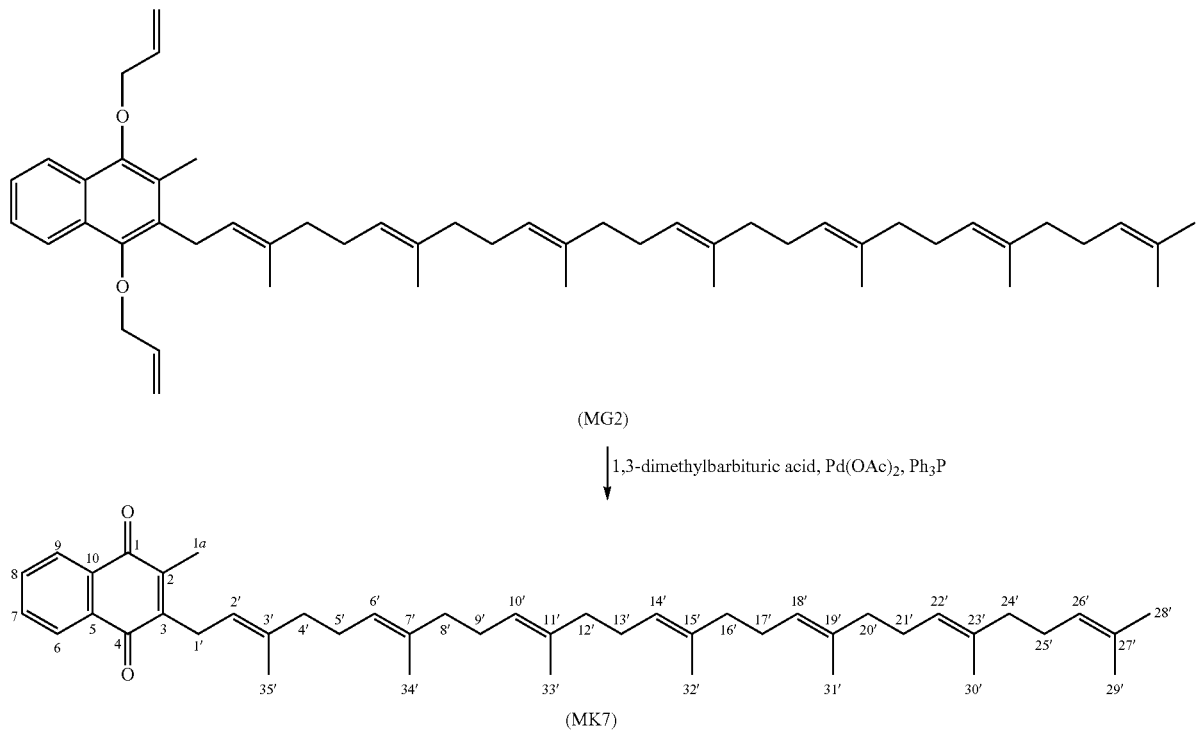

(MG2)

↓ 1,3-dimethylbarbituric acid, Pd(OAc)$_2$, Ph$_3$P (MK7)

1,3-Dimethylbarbituric acid (96 mg, 0.62 mM), Pd(OAc)$_2$ (38 mg, 0.17 mM) and Ph$_3$P (40 mg, 0.15 mM) were added to the solution of MG2 (100 mg, 0.137 mM) in acetonitrile (3 mL) and DCM (2 mL). The mixture was stirred for 30 min at 35° C., then the solution was filtered through a Celite and DCM (10 mL) was added. The filtrate was washed with water, and the organic phase was concentrated to give the orange oil. The crude product was purified by column chromatography (hexane/ethyl acetate 20:1) to afford an oily product MK-7 (81 mg, 92%). The product was crystallized in ethyl acetate and ethanol, and vitamin MK-7 was obtained as the yellow solid (79 mg). NMR consistent with Example 15 data.

The invention claimed is:

1. A process of preparation of vitamin K$_2$ derivatives, represented by formula (I)

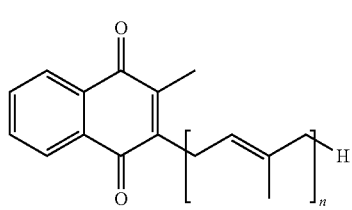

(I)

wherein n is an integer from 3 to 13,
comprising the steps of:
  (a) reacting an α-sulfonyl carbanion generated in situ from a phenylsulfone of menadiol derivative of formula (II)

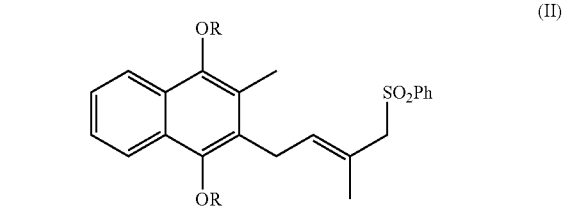

(II)

wherein R represents an allyl protecting group,
in the presence of an organometallic base,
with a polyprenyl halide of formula (VII)

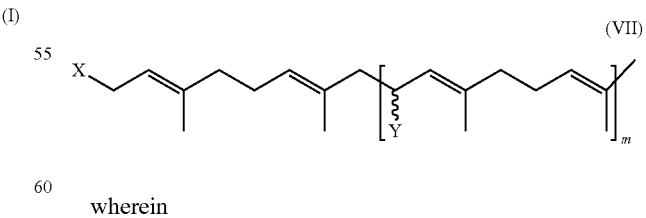

(VII)

wherein
X is a halogen atom selected from the group consisting of bromine, chlorine and fluorine atoms,
Y is H or —SO$_2$Ph,
m is an integer from 0 to 5,
as an alkylating agent;

to yield a phenylsulfonyl derivative of menadiol of formula (VIII)

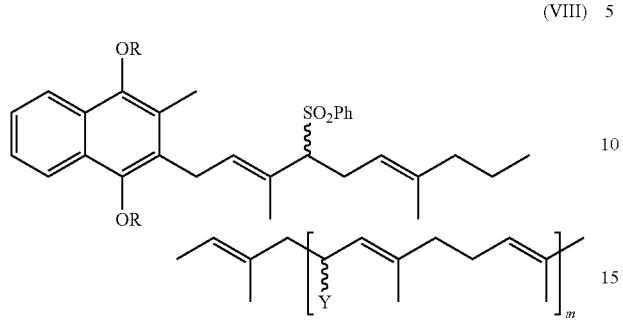

(VIII)

wherein R, Y, and m have the meaning defined above,
(b) removing the phenylsulfonyl groups from the menadiol derivative of formula (VIII) by reductive elimination, to yield a menadiol derivative of formula (IX)

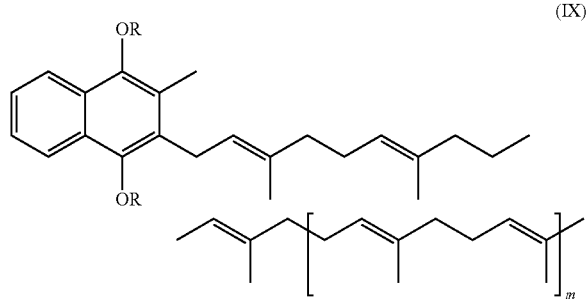

(IX)

wherein R and m have the meaning defined above;
(c) subjecting the menadiol derivative of formula (IX) to an oxidative deeterification, to yield a crude menadione compound of formula (I),

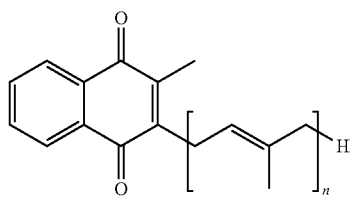

(I)

wherein
n is the integer from 3 to 13, and
(d) optionally, purifying the crude menadione compound of formula (I) to yield pure vitamin $K_2$.

2. The process according to claim 1, wherein the α-sulfonyl carbanion is generated by means of an alkali metal hexamethyldisilazyde in a polar aprotic solvent.

3. The process according to any of the preceding claims, wherein phenylsulfonyl groups are removed with sodium amalgam in MeOH, buffered with $Na_2HPO_4$.

4. The process according to any of the preceding claims, wherein the oxidative deesterification is accomplished with the use of $Pd(OAc)_2/Ph_3P$ and 1,3-dimethylbarbituric acid.

5. The process according to any of the preceding claims, wherein the alkylating agent in (a) is the polyprenyl halide of formula (VII)

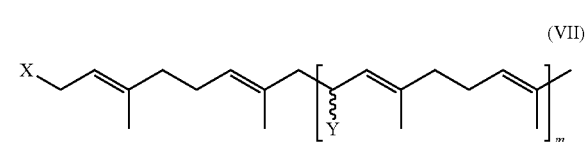

(VII)

wherein
X is a halogen atom selected from the group consisting of bromine, chlorine and fluorine atoms,
Y is —$SO_2Ph$,
m is an integer from 0 to 5.

6. The process according to any of the preceding claims, wherein the alkylating agent in (a) is the polyprenyl halide of formula (VII)

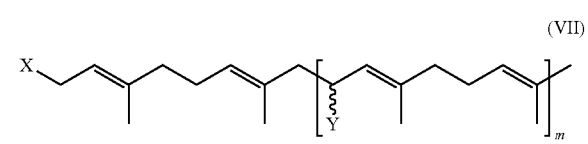

(VII)

wherein
X is a bromine atom,
Y is —$SO_2Ph$, and
m is an integer from 0 to 5.

7. The process according to any of the preceding claims, wherein the polyprenyl halide used as the alkylaing agent is obtained in a stepwise process of:
(i) coupling a phenylsulfonyl-geranyl unit of formula (III),

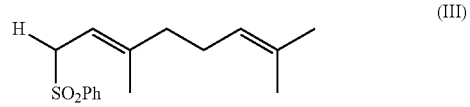

(III)

with a compound of formula (IV)

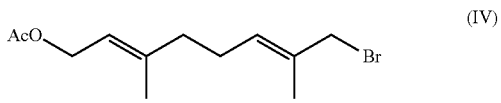

(IV)

and repeating said coupling process with the use of compound of formula (IV) until a compound of formula (V) of desired chain length m is obtained

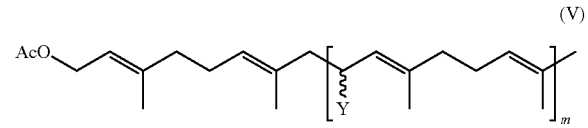

(V)

wherein
Y is —$SO_2Ph$,
m is an integer from 1 to 4;

(ii) hydrolysis of the compound of formula (V), to yield a polyisoprenol derivative of formula (VI)

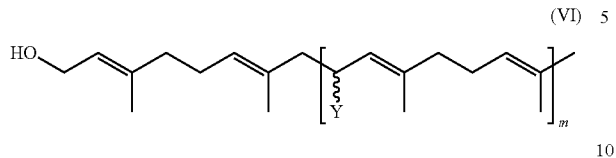

wherein Y is —SO$_2$Ph, and m is an integer from 0 to 5;

(iii) optionally, removing the phenylsulfonyl groups to yield a polyisoprenol derivative of formula (VI)

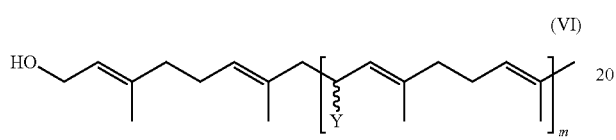

wherein Y is H, and m is defined above, and (iv) substituting the hydroxyl group of the compound of formula (VI) for a halogen atom selected from the group consisting of bromine, chlorine, an fluorine atoms in a reaction with a halogenating agent, to yield a polyprenyl halide of formula (VII),

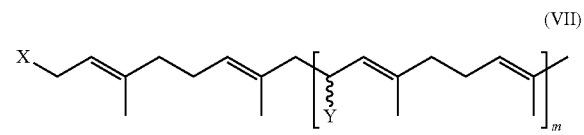

wherein X is a halogen atom selected from the group consisting of bromine, chlorine and fluorine atoms, Y is H or —SO$_2$Ph, and m is defined above.

8. The process according to any of the preceding claims, wherein MK-7 type of vitamin K2 is obtained.

9. New menadiol phenylsulfone compound of formula (II)

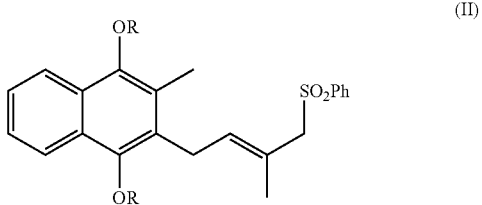

wherein R is an allyl protecting group.

10. A process of preparation of the menadiol phenylsulfone of formula (II)

wherein R of formula (II) represents the allyl protecting group, in a Friedel-Crafts reaction catalysed by a Lewis acid, wherein InCl$_3$ is used as the Lewis acid in the presence of a solid inorganic base as an alkylation promoter.

11. The process according to claim 10, wherein Na$_2$CO$_3$ or K$_2$CO$_3$ is used as the solid inorganic base.

12. An intermediate compounds selected from the group comprising of:

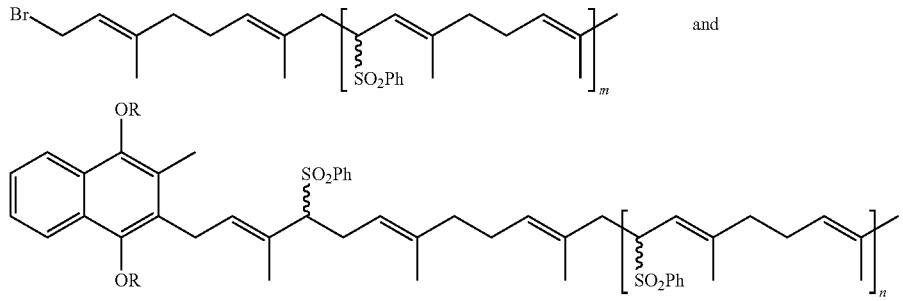

wherein

R is an allyl protecting group, m is an integer from 0 to 5, and n is an integer from 0 to 5.

13. The process according to claim 2, wherein the alkali metal hexamethyldisilazide is sodium hexamethyldisilazyde.

14. The process according to claim 2, wherein the polar aprotic solvent is selected from the group consisting of tetrahydrofuran, dimethylformamide, hexamethylphosphoramide, and mixtures thereof.

15. The intermediate compound of claim 12, wherein said intermediate compound is:

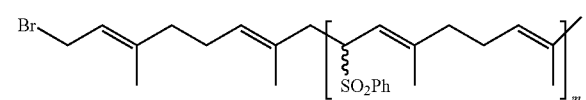

wherein m is an integer from 1 to 5.

16. The intermediate compound of claim 12, wherein said intermediate compound is:

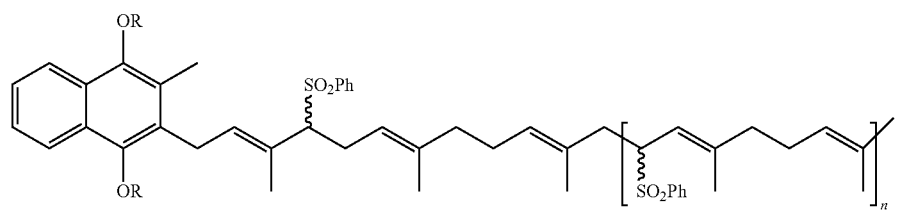
wherein
R is an allyl protecting group, and
n is an integer from 0 to 5.
17. The process according to claim 1, wherein (d) occurs.
18. The process according to claim 7, wherein (iii) occurs.
* * * * *